US011834648B2

(12) United States Patent
Yan et al.

(10) Patent No.: US 11,834,648 B2
(45) Date of Patent: Dec. 5, 2023

(54) HUMAN INDUCED PLURIPOTENT STEM CELL LINES FOR MODELING ALZHEIMER'S DISEASE AND USAGE THEREOF

(71) Applicant: SHENZHEN CELL INSPIRE BIOTECHNOLOGY CO., LTD., Guangdong (CN)

(72) Inventors: Yubo Yan, Shenzhen (CN); Jian Fu, Jingshan Country (CN); Min Zhou, Huaji County (CN); Yuqing Liu, Shenzhen (CN); Lixiang Jiang, Shenzhen (CN); Bo Yang, Wuhan (CN); Jiayin Yang, Guangzhou (CN)

(73) Assignee: Shenzhen Cell Inspire Biotechnology Co., Ltd., Guangdong (CN)

( * ) Notice: Subject to any disclaimer, the term of this patent is extended or adjusted under 35 U.S.C. 154(b) by 529 days.

(21) Appl. No.: 16/761,935

(22) PCT Filed: Nov. 6, 2017

(86) PCT No.: PCT/CN2017/109547
§ 371 (c)(1),
(2) Date: May 6, 2020

(87) PCT Pub. No.: WO2019/084958
PCT Pub. Date: May 9, 2019

(65) Prior Publication Data
US 2021/0180029 A1 Jun. 17, 2021

(51) Int. Cl.
*C12N 5/074* (2010.01)
*C12N 5/0793* (2010.01)
*C12N 15/90* (2006.01)
*G01N 33/50* (2006.01)
*G01N 33/68* (2006.01)

(52) U.S. Cl.
CPC ......... *C12N 5/0696* (2013.01); *C12N 5/0619* (2013.01); *C12N 15/90* (2013.01); *G01N 33/5058* (2013.01); *G01N 33/6896* (2013.01); *C12N 2503/02* (2013.01); *C12N 2506/025* (2013.01); *C12N 2506/45* (2013.01); *C12N 2510/00* (2013.01); *C12N 2740/10043* (2013.01); *G01N 2333/4709* (2013.01)

(58) Field of Classification Search
CPC .... C12N 5/0696; C12N 5/0619; C12N 15/90; C12N 2503/02; C12N 2506/025; C12N 2506/45; C12N 2510/00; C12N 2740/10043; C12N 2506/25; G01N 33/5058; G01N 33/6896; G01N 2333/4709; G01N 2800/2821
See application file for complete search history.

(56) References Cited

U.S. PATENT DOCUMENTS

| 2002/0157122 | A1 | 10/2002 | Wong | |
|---|---|---|---|---|
| 2016/0074535 | A1* | 3/2016 | Ranganathan | ..... C12N 15/8616 435/325 |
| 2017/0035860 | A1 | 2/2017 | Flynn | |

FOREIGN PATENT DOCUMENTS

| CN | 105596349 A | 5/2016 |
|---|---|---|
| JP | 2012523232 A | 10/2012 |
| JP | 2015516162 A | 6/2015 |
| WO | 2004076661 A1 | 9/2004 |
| WO | 2010117464 A1 | 10/2010 |
| WO | 2011046189 A1 | 4/2011 |
| WO | 2013169802 A1 | 11/2013 |
| WO | WO2019084958 A1 | 5/2019 |

OTHER PUBLICATIONS

Yang et al. Oncotarget, 8:7900-13, published online Dec. 2, 2016 (Year: 2016).*
System Biosciences manual: "AAVS1 Safe Harbor Targeting System" (2015) (Year: 2015).*
Abe, Y. et al. (Sep. 17, 2003). "Analysis of Neurons Created From Wild-Type and Alzheimer's Mutation Knock-In Embryonic Stem Cells By a Highly Efficient Differentiation Protocol," J. Neurosci. 23(24):8513-8525.
Doege, C.A. et al. (Jan. 27, 2014). "Dementia in a Dish," Biological Psychiatry 75(7):558-564.
Plucińska, K. et al. (Aug. 6, 2014). "Knock-In of Human BACE1 Cleaves Murine APP and Reiterates Alzheimer-Like Phenotypes," The Journal of Neuroscience 34(32):10710-10728.
Wang, C. et al. (Oct. 10, 2017). "Scalable Production of iPSC-Derived Human Neurons to Identify Tau-Lowering Compounds by High-Content Screening," Stem Cell Reports 9(4):1221-1233.
Woodruff, G. et al. (Nov. 27, 2013). "The Presenilin-1 ΔE9 Mutation Results in Reduced γ-Secretase Activity, but Not Total Loss of PS1 Function, in Isogenic Human Stem Cell," Cell Reports 5(4):974-985.
Alexopoulou, A. et al. (Jan. 11, 2008). "The CMV Early Enhancer/Chicken Beta Actin (CAG) Promoter Can Be Used to Drive Transgene Expression During The Differentiation of Murine Embryonic Stem Cells Into Vascular Progenitors," BMC Cell Biology 9:2, 11 pages.
Bertram, L. et al. (2009). "Genome-wide Association Studies In Alzheimer Disease," Human Molecular Genetics. 18(2):R137-R145.

(Continued)

*Primary Examiner* — Kimberly Ballard
*Assistant Examiner* — Stacey N MacFarlane
(74) *Attorney, Agent, or Firm* — Morrison & Foerster LLP

(57) ABSTRACT

A method of generating a cellular model of Alzheimer's disease (AD) comprises integrating AD related gene to hiPSC to induce increased beta secretase and/or Abeta 42 peptides, and the cellular model of Alzheimer's disease (AD) is prepared by the method.

13 Claims, 15 Drawing Sheets

Specification includes a Sequence Listing.

(56) References Cited

OTHER PUBLICATIONS

Blennow, K. et al. (Jul. 29, 2006). "Alzheimer's Disease" Lancet. 368(9533):387-403. Abstract Only, 1 page.
Chen, Y. et al. (Aug. 15, 2012). "Alzheimer's β-Secretase (BACE1) Regulates The CAMP/PKA/CREB Pathway Independently of β-Amyloid," The Journal of Neuroscience 32(33):11390-11395.
Cong, L. et al. (Feb. 15, 2013). "Multiplex Genome Engineering Using CRISPR/Cas Systems," Science 339(6121):819-823, 9 pages.
Crews, L. et al. (2010, e-pub. Apr. 22, 2010). "Molecular Mechanisms of Neurodegeneration In Alzheimer's Disease," Hum. Mol. Genet. 19(R1):R12-R20.
Evin, G. et al. (2013, e-pub Jul. 11, 2013). "BACE1 as a Therapeutic Target in Alzheimer's Disease: Rationale and Current Status," Drugs Aging 30(10):755-764.
Fukumoto, H. et al. (Sep. 2002). "β-Secretase Protein and Activity Are Increased in the Neocortex in Alzheimer Disease," Arch Neurol 59:1381-1389.
Gatz, M. et al. (2006). "Role of Genes and Environments for Explaining Alzheimer Disease," Arch. Gen. Psychiatry. 63(2)168-174.
Ghosh, A.K. et al. (Jan. 2012). "Developing β-Secretase Inhibitors for Treatment of Alzheimer's Disease," J Neurochem 120(Suppl 1):71-83.
Ghosh, A.K. et al. (Sep. 2015). "Prospects of β-Secretase Inhibitors for the Treatment of Alzheimer's Disease," Chem Med Chem 10(9):1463-1466, 8 pages.
Guerreiro, R. et al. (Jan. 10, 2013). "TREM2 Variants in Alzheimer's Disease," The New England Journal of Medicine 368(2):117-127, 14 pages.
Habchi, J. et al. (2016). "Identification of Novel Aβ Inhibitors," Proc. Natl. Acad. Sci. USA 114:E200-E208, Abstract, 1 page.
Habchi, J. et al. (2016, e-pub. Dec. 23, 2016). "Systematic Development of Small Molecules to Inhibit Specific Microscopic Steps of Aβ42 Aggregation in Alzheimer's Disease," Proc. Natl Acad. Sci. USA 114:E200-E208, 9 pages.
Higgins, G.A. et al. (Sep. 2003). "Transgenic Mouse Models of Alzheimer's Disease: Phenotype and Application," Behavioural Pharmacology 14:419-438, Abstract Only, 2 pages.
Hsu, P.D. et al. (Jun. 5, 2014). "Development and Applications of CRISPR-Cas9 for Genome Engineering," Cell 157:1262-1278.
International Search Report and Written Opinion, dated Jul. 31, 2018, for PCT Application No. PCT/CN2017/109547, filed Nov. 6, 2017, 9 pages.
Israel, M.A. et al. (Aug. 9, 2012). "Probing Sporadic and Familial Alzheimer's Disease Using Induced Pluripotent Stem Cells," Nature 482:216-220, 14 pages.
Jankowsky, J.L. et al. (2004, e-pub. Nov. 25, 2003). "Mutant Presenilins Specifically Elevate the Levels of the 42 Residue β-Amyloid Peptide in vivo: Evidence for Augmentation of a 42-Specific γ Secretase," Human Molecular Genetics 13(2):159-170.
Jonsson, T. et al. (Jan. 10, 2013). "Variant of TREM2 Associated With the Risk of Alzheimer's Disease," The New England Journal of Medicine. 368(2):107-116, 15 pages.
Kondo, T. et al. (Apr. 4, 2013). "Modeling Alzheimer's Disease With iPSCs Reveals Stress Phenotypes Associated With Intracellular Ab and Differential Drug Responsiveness," Cell Stem Cell 12:487-496.
Li, R. et al. (Mar. 9, 2004). "Amyloid Beta Peptide Load Is Correlated With Increased β-Secretase Activity in Sporadic Alzheimer's Disease Patients," Proc Natl Acad. Sci. USA 101(10):3632-3637.
Mahley, R.W. et al. (Apr. 11, 2006). "Apolipoprotein E4: A Causative Factor and Therapeutic Target In Neuropathology, Including Alzheimer's Disease," Proc. Nat. Acad. Sci. USA 103(15):5644-5651.
McBurney, M.W. et al. (Oct. 25, 1991). "The Mouse Pgk-1 Gene Promoter Contains an Upstream Activator Sequence," Nucleic Acids Res. 19(20):5755-5761.

Menting, K.W. et al. (Jul. 21, 2014). "β-Secretase Inhibitor; A Promising Novel Therapeutic Drug in Alzheimer's Disease," Front Aging Neurosci 6(165):1-9.
Michel, G. et al. (Nov. 3, 2006). "A Century of Alzheimer's Disease. Science," 314:777-781.
Muratore, C.R. et al. (2014, e-pub. Feb. 12, 2014). "The Familial Alzheimer's Disease APPV717I Mutation Alters APP Processing and Tau Expression in iPSC-Derived Neurons," Hum Mol Genet. 23(13):3523-3536.
Musiek, E.S. et al. (Jun. 2015). "Three Dimensions of the Amyloid Hypothesis: Time, Space, and 'Wingmen'," Nat Neurosci 18(6):800-806, 17 pages.
Nie, Q. et al. (2011, e-pub. Apr. 18, 2011). "Small Molecule Inhibitors of amyloid β Peptide Aggregation as a Potential Therapeutic Strategy for Alzheimer's Disease," Acta Pharmacologica Sinica 32 545-551.
Okabe, M. et al. (May 5, 1997). "'Green Mice' as a Source of Ubiquitous Green Cells," FEBS Lett. 407(3):313-319.
Ran, F.A. et al. (Nov. 2013). "Genome Engineering Using the CRISPR-Cas9 System," Nature Protocols 8(11):2281-2308, 49 pages.
Selkoe, D.J. (Jun. 24, 1999). "Translating Cell Biology Into Therapeutic Advances in Alzheimer's Disease," Nature 399(6738 Suppl):A23-A31.
Sproul, A.A. et al. (Jan. 8, 2014). "Characterization and Molecular Profiling of PSEN1 Familial Alzheimer's Disease iPSC-Derived Neural Progenitors," PLOS ONE 9(1):e84547, 11 pages.
Strittmatter, W.J. et al. (Mar. 1993). "Apolipoprotein E: High-Avidity Binding to Beta-Amyloid and Increased Frequency of Type 4 Allele in Late-Onset Familial Alzheimer Disease," Proc. Nat. Acad. Sci. U.S.A. 90(5):1977-1981.
Takahashi, K. et al. (Aug. 25, 2006). "Induction of Pluripotent Stem Cells From Mouse Embryonic and Adult Fibroblast Cultures by Defined Factors," Cell 126(4):663-676.
Takahashi, K. et al. (Nov. 30, 2007). "Induction of Pluripotentstem Cells From Adult Human Fibroblasts By Defined Factors," Cell 131(5):861-872.
Tanzi, R.E. et al. (Feb. 25, 2005). "Twenty Years of the Alzheimer's Disease Amyloid Hypothesis: A Genetic Perspective," Cell 120:545-555.
Vassar, R. (2014). "BACE1 Inhibitor Drugs in Clinical Trials for Alzheimer's Disease," Alzheimer's Research & Therapy 6:89, 14 pages.
Wang, J. et al. (2015). "Generation of Clinical-Grade Human Pluripotent Stem Cells in Xeno-Free Conditions," Stem Cell Research & Therapy (6):223, 11 pages.
Willem, M. et al. (Oct. 27, 2006). "Control of Peripheral Nerve Myelination By The β-Secretase BACE1," Science 314(5799):664-666.
Wilson, R. S. et al. (2011). "Heritability of Different Forms of Memory in the Late Onset Alzheimer's Disease Family Study," Journal Alzheimer's Disease. 23(2):249-255, 11 pages.
Yagi, T. et al. (2011, e-pub. Sep. 7, 2011). "Modeling Familial Alzheimer's Disease With Induced Pluripotent Stem Cells," Human Molecular Genetics 20(23):4530-4539.
Yang, J. et al. (Dec. 31, 2016). "Induced Pluripotent Stem Cells in Alzheimer's Disease: Applications for Disease Modeling and Cell-Replacement Therapy," Molecular Neurodegeneration 11(39):1-11.
Yang, L.B. et al. (Jan. 2003). "Elevated β-Secretase Expression and Enzymatic Activity Detected in Sporadic Alzheimer Disease," Nat Med. 9(1):3-4.
Young, J.E. et al. (2012, e-pub. Aug. 2, 2012). "Alzheimer's Disease in a Dish: Promises and Challenges of Human Stem Cell Models," Hum. Mol. Genet. 21(R1):R82-R89.
Young, J.E. et al. (Apr. 2, 2015). "Elucidating Molecular Phenotypes Caused By the SORL1 Alzheimer's Disease Genetic Risk Factor Using Human Induced Pluripotent Stem Cells," Cell Stem Cell 16(4):373-385.
Zhou, T. et al. (Dec. 2012, e-pub. Nov. 8, 2012). "Generation of Human Induced Pluripotent Stem Cells From Urine Samples," Nat Protoc. 7(12):2080-2089.

\* cited by examiner

E

F

A.

B.

C.

A.

B.

C.

A.

B.

D.

A.

B.

A.

B.

C.

HUMAN INDUCED PLURIPOTENT STEM CELL LINES FOR MODELING ALZHEIMER'S DISEASE AND USAGE THEREOF

CROSS REFERENCE TO RELATED APPLICATIONS

This application is a National Phase application under 35 U.S.C. § 371 of International Application No. PCT/CN2017/109547, filed Nov. 6, 2017, the disclosures of which are herein incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 794922001700subseqlisting.txt, date recorded: May 8, 2023, size: 34,635 bytes).

FIELD

The present disclosure relates to biomedical field, particularly to creation of physiologically relevant cellular models for Alzheimer's disease (AD). Specifically, the present invention relates to a method for preparing a cellular model of AD by genetically modifying human induced pluripotent stem cell (hiPSC).

BACKGROUND

Alzheimer's disease (AD) is a chronic neurodegenerative disease and the most common cause of dementia. The genetic heritability of Alzheimer's disease, based on reviews of twin and family studies, ranges from 49% to 79% (ref 1-2). Around 0.1% of the cases are familial forms of autosomal (not sex-linked) dominant inheritance, which have an onset before age 65 (ref 3). This form of the disease is known as early onset familial Alzheimer's disease. Most of autosomal dominant familial AD can be attributed to mutations in one of three genes: those encoding amyloid precursor protein (APP) and presenilins 1 and 2 (ref 4). Most mutations in the APP and presenilin genes increase the production of a small protein called A342, which is the main component of senile plaques (ref 5).

Most cases of Alzheimer's disease do not exhibit autosomal-dominant inheritance and are termed sporadic AD, in which environmental and genetic differences may act as risk factors. The best known genetic risk factor is the inheritance of the ε4 allele of the apolipoprotein E (APOE) (ref 6-7). Between 40 and 80% of people with AD possess at least one APOEε4 allele (ref 7). The APOEε4 allele increases the risk of the disease by three times in heterozygotes and by 15 times in homozygotes (ref 3).

Mutations in the TREM2 gene have been associated with a 3 to 5 folds higher risk of developing Alzheimer's disease (ref 8-9). A suggested mechanism of action is that when TREM2 is mutated, white blood cells in the brain are no longer able to control the amount of beta amyloid present.

AD is characterized by two distinct features: one is presence of extracellular plaques containing amyloid β-protein (Aβ), and the other is intracellular neurofibrillary tangles (NFTs). Although the true pathology of AD is still not clear, accumulated knowledge from decades of research has provided strong evidence for the amyloid cascade hypothesis. According to this hypothesis, the key event leading to AD appears to be the formation of a specific peptide during the process of amyloid precursor protein (APP). This peptide, known as amyloid beta peptide 42 (Aß-42), is a sticky peptide that can easily aggregate to form $Aß_{42}$ oligomers and subsequently amyloid plaques, the first feature of AD. Presence of $Aß_{42}$ aggregates and amyloid plaques can trigger inflammation in neurons and increase expression of calcium-activated kinases that, in turn, induce excessive phosphorylation of tau protein, a protein that stabilizes the cytoskeletal microtubules in neurons. Hyperphosphorylation of tau protein leads to formation of neurofibrillary tangles in neurons, the second feature of AD, and subsequently causes neuron death (ref 10-14).

Three enzymes, α-secretase, β-secretase, and γ-secretase, are involved in cleavage of APP. In normal process, APP is first cleaved by either α-secretase or β-secretase, whereas γ-secretase will further process the cleaved products into a mixture of peptides with different lengths. If APP is cleaved by β-secretase, the products will be further cleaved by γ-secretase to produce either a 40 amino acid amyloid peptide (Aβ40) which is soluble or a 42 amino acid peptide ($Aβ_{42}$) which clumps together to form insoluble aggregates and thus amyloid plaques. Strong evidence for amyloid cascade hypothesis comes from studies of familial AD (FAD), which show that all familial AD patients have mutation in either APP or Presenilin (PS) gene. The mutations in APP gene result in abnormal APP protein that is preferentially cleaved by beta-secretase to produce more Abeta peptides; whereas mutations in PS genes leads to preferentially production of Abeta42 peptide, the constituent of amyloid plaques. Another important observation is that beta-secretase expression and the enzyme activity is significantly elevated in AD patients, particularly in sporadic AD (SAD) patients that represent greater than 90% of AD population. The beta-secretase protein and activity levels are increased in brain regions affected by amyloid deposition and remain increased despite significant neuronal and synaptic loss in AD (ref 15-17).

Beta-secretase 1 (BACE1), also known as beta-site amyloid precursor protein cleaving enzyme 1, beta-site APP cleaving enzyme 1, membrane-associated aspartic protease 2, memapsin-2, aspartyl protease 2, and ASP2, is an aspartic-acid protease important in the formation of myelin sheaths in peripheral nerve cells (ref 18). In humans it is encoded by the BACE1 gene. Extracellular cleavage of APP by BACE1 creates a soluble extracellular fragment and a cell membrane-bound fragment referred to as C99. Cleavage of C99 within its transmembrane domain by γ-secretase releases the intracellular domain of APP and produces amyloid-β. Since gamma-secretase cleaves APP closer to the cell membrane than BACE1 does, it removes a fragment of the amyloid-β peptide. Initial cleavage of APP by α-secretase rather than BACE1 prevents eventual generation of amyloid-β.

Unlike APP and the Presenilin (PS) proteins, no known mutations in the gene encoding BACE1 cause early-onset, familial Alzheimer's disease, which is a rare form of the disorder. However, levels of this enzyme have been shown to be elevated in the far more common late-onset sporadic Alzheimer's. The physiological purpose of BACE's cleavage of APP and other transmembrane proteins is unknown. BACE2 is a close homolog of BACE1 with no reported APP cleavage in vivo.

Since production of Abeta-42 peptides play a major role in formation of amyloid plaques, all drug development effort in the past two decades or so have been focused on reduction of Abeta-42 peptides, either through inhibition of beta-secretase activity or by inhibition of Abeta-42 aggregation (ref 19-26). However, one of the major problems for AD drug development is lack of suitable AD models. The most known AD model so far is the 5×FAD transgenic mouse that is created by inserting mutant APP and PS1 genes into mouse genome to display AD phenotype in aged mice (ref 27). Although widely used, the 5×FAD mouse model has two major drawbacks regarding its utility in drug development. First, the human central nervous system is very different from that of mouse and thus drug candidates tested on the 5×FAD model usually have poor predictability for their effect on human. Second, it takes six to eight months or longer for 5×FAD mouse to develop phenotype so this model is obviously not suitable for early screening of AD drug candidates.

Pluripotent stem cells hold great promise in preparing cellular model for they can propagate indefinitely, as well as give rise to every other cell type in the body, such as neurons, heart, pancreatic, and liver cells. Human induced pluripotent stem cell (hiPSC), is a type of pluripotent stem cell that can be generated directly from adult cells. The iPSC technology was pioneered by Shinya Yamanaka's lab in Kyoto, Japan, who showed in 2006 that the introduction of four specific genes encoding transcription factors could convert adult cells into pluripotent stem cells. This breakthrough technology is called somatic cell reprogramming technology that enables researchers to convert terminally differentiated cells such as skin fibroblasts back to embryonic stem cell stage (ref 28-29).

hiPSC can be obtained from patients with all kinds of diseases and be propagated indefinitely and therefore provide unlimited cell source. More importantly, those patient-derived hiPSC can be re-differentiated into disease-relevant primary cells and display disease phenotype at cellular level (ref 30-36). This constitutes one common strategy for creation of hiPSC-based cellular disease model. The strategy is to generate hiPSC from patients who are clearly diagnosed with a disease and then differentiate the patient-derived hiPSC into targeted cell type to display the disease phenotype in vitro.

Besides the patient-derived hiPSC, researchers have been experimenting another strategy to establish cellular disease models. They generate hiPSC from non-diseased person and then introduce disease-causing genes into hiPSC by genome editing technology.

In order to make a suitable cellular model of AD from hiPSC, it has to meet several criteria: it has to be physiologically equivalent to human functional neurons; it has to display AD phenotype in vitro in a relatively short period of time; and it has to be feasible to make large quantities of AD-relevant human neurons consistently and reproducibly. Despite decades of research, there was no real success to make such a cellular model.

SUMMARY

The present invention satisfies at least some of the aforementioned needs by providing a method of preparing a cellular model of Alzheimer's disease (AD), comprising genetically modifying the hiPSC to produce higher levels of beta-secretase and beta-42 peptide compared to those isogenic hiPSC from which the cellular model is derived.

For the present disclosure, the inventors introduced AD-related genes into non-diseased hiPSC resulting in isogenic lines, i.e. the diseased cell line and the non-diseased cell line have the same genetic background, and the diseased cell line manifests AD phenotype at cellular level in vitro in a relatively short period of time because of the stacking effect of AD-related genes introduced by genome editing technology.

In one aspect, the present invention provides a method of generating a cellular model of Alzheimer's disease (AD), comprising integrating AD-related gene to hiPSC to induce increased beta-secretase level and/or Abeta-42 peptides. In one embodiment, the AD-related gene is constitutively overexpressed in hiPSC. In one embodiment, the AD-related gene is mutant APP or PS gene attributing to the onset of AD, especially PS1dE9 gene. In one embodiment, the AD-related gene is BACE1 gene. In one embodiment, the AD-related gene is selected from the group consisting of mutant APP attributing to the onset of AD, PS1dE9 gene and BACE1 gene.

In certain embodiments, the AD-related gene is integrated into hiPSC by a site-specific manner. Preferably, the AD-related gene is integrated into hiPSC at AAVS1 site.

In one aspect, the present invention provides the cellular model of Alzheimer's disease (AD) generated by above methods.

In one aspect, the present invention encompasses a method of modifying hiPSC, comprising introducing an AD-related gene into hiPSC to make it constitutively overexpressed. In one embodiment, the AD-related gene is introduced to the hiPSC by an expression vector comprising a nucleotide acid sequence encoding an AD-related protein and a reporter, wherein the nucleotide acid sequence operably linked with a promoter for driving high level of gene expression in a mammalian expression vector. In one embodiment, the promoter is PGK-1 promoter or CAG promoter. In one embodiment, a drug selection gene controlled by a promoter for driving high level of gene expression in a mammalian expression vector is further introduced into the hiPSC in the same expression vector comprising the nucleotide acid sequence encoding an AD-related protein and a reporter or in a separate expression vector. In one embodiment, the promoter is PGK-1 promoter or CAG promoter. In one embodiment, the expression vector further comprises a nucleotide acid sequence for site specific integration, preferably, a nucleotide acid sequence homologous to human AAVS1 site. In one aspect, the present invention provides an expression vector comprising a nucleotide acid sequence encoding an AD-related protein and a reporter, wherein the nucleotide acid sequence operably linked with a promoter for driving high level of gene expression in a mammalian expression vector. In one embodiment, the promoter is PGK-1 promoter or CAG promoter. In one embodiment, the vector further comprises a nucleotide acid sequence encoding a drug selection gene controlled by a promoter for driving high level of gene expression in a mammalian expression vector. In one embodiment, the promoter is PGK-1 promoter or CAG promoter. In one embodiment, the vector further comprises a nucleotide acid sequence for site specific integration, preferably, a nucleotide acid sequence homologous to human AAVS1 site. In one embodiment, the drug selection gene is antibiotic resistance gene, preferably, puromycine, neomycine, kanamycine, or geneticine resistance gene. In one embodiment, the reporter gene is a gene encoding green fluorescent protein or red fluorescent protein. In one embodiment, all the elements in the vector is in an order beneficial to expression of the AD-related gene. Preferably, all the elements in the vector is in a cis order.

In an aspect, the present invention provides a genetic construct, comprising a nucleic acid sequence coding for: a first promoter; a drug selection gene controlled by the first promoter; a second promoter; an AD-related gene linked with a reporter gene controlled by the second promoter; and sequence homologous to human AAVS1 site, wherein all said elements are in a cis order. In one embodiment, the first promoter is human PGK-1 or CAG promoter; the drug selection gene is antibiotic resistance gene; the second promoter is human PGK-1 or CAG promoter; the AD-related gene is BACE1 and the reporter gene is a gene encoding green fluorescent protein or red fluorescent protein, preferably, a gene encoding green fluorescent protein. In one embodiment, the first promoter is human PGK-1 or CAG promoter; the drug selection gene is antibiotic resistance gene; the second promoter is human PGK-1 or CAG promoter; the AD-related gene is PS1dE9 and the reporter gene is GFP. In one embodiment, the antibiotic resistance gene is puromycine, neomycine, kanamycine, or geneticine resistance gene. In one aspect, the present invention provides a modified hiPSC line transformed by any one of the expression vector as stated above, or any one of the genetic construct as stated above. In one embodiment, the hiPSC line is used for generating cellular AD model.

In one aspect, the present invention provides a genetically modified hiPSC for use as a cellular model of AD, which is integrated BACE1 gene at the human AAVS1 site and constitutively overexpresses the integrated BACE1 gene. In one embodiment, the modified hiPSC displays increased beta-secretase level and/or Abeta-42 peptides compared to an isogenic hiPSC without the integration of the BACE1 gene. In one embodiment, the modified hiPSC is integrated PS1dE9 gene at the human AAVS1 site and constitutively overexpresses the integrated PS1dE9 gene.

In one aspect, the present invention encompasses the use of the genetically modified hiPSC for high throughput screening of a drug for AD treatment.

In one aspect, the present invention provides a high throughput method for screening a therapeutic agent for treatment of AD, comprising
i) Preparing a cellular model of Alzheimer's disease (AD) from a hiPSC by introducing the expression vector as above stated or the genetic construct as above stated to the hiPSC,
ii) Culturing the candidate compounds with the cellular model for two days to two weeks,
iii) Measuring beta-secretase level, Abeta-42 concentration, and Abeta-42/Abeta-40 ratio before and after adding the candidate compounds; and
iv) Reduction of one or more measurements selected from beta-secretase level, Abeta-42 concentration and Abeta-42/Abeta-40 ratio indicates the candidate compound is a potential therapeutic agent for treatment of AD.

In one embodiment, the hiPSCs come from a human donor and are converted to hiPSC by a conventional reprogramming method in vitro. In one embodiment, the method is for screening of early AD drug.

In one aspect, the present invention provides a drug screening process for screening beta-secretase or Abeta-42 inhibitor, comprising
i) Modifying hiPSC line by constitutively over-expressing BACE1 gene or PS1dE9 gene,
ii) Re-differentiating hiPSC line into functional neurons,
iii) Culturing the functional neurons in presence of candidate drug compounds, and
iv) Measuring beta-secretase level and/or Abeta-42 concentration and selecting compounds that can reduce beta-secretase level and/or Abeta-42 concentration.

In an embodiment, the method comprises culturing the functional neurons in presence of candidate drug compounds for two days to two weeks.

BRIEF DESCRIPTION OF THE DRAWINGS

These and other aspects and advantages of embodiments of the present disclosure will become apparent and more readily appreciated from the following descriptions made with reference the accompanying drawings, in which:

FIG. 1A. The process of reprogramming of urine cells, showing morphological changes and alkanin phosphotase (AP) staining; FIG. 1B. Immunostaining of biomarkers for pluripotent stem cells (Nanog, Tra-1-60, Tra-1-81, SSEA3, and SSEA4); FIG. 1C-1E. Additional pluripotency test (transgene silencing, expression of endogenous pluripotency genes, FACS of surface markers, promoter demythelation, karyotyping, embryoid body formation and expression of germ layer markers); and FIG. 1F. Teratoma formation, showing three germ layers.

FIG. 3A. The backbone vector CIB-PCBEB; FIG. 3B. Donor vector for targeted integration of BACE1 gene; and FIG. 3C. Donor vector for targeted integration of PS1dE9 gene.

FIG. 4A. The targeted integration strategy; FIG. 4B. Screening of single cell clones by junction PCR (upper panel: 5'end junction PCR using F1+R1 primers. The clone 21 is iPSN0041-21 with insert and the clone 24 is a negative clone without insert; lower panel: 3' end junction PCR); FIG. 4C. Sequences of 5'end and 3'end of the insert in iPSN0041-21.

FIG. 5A. The targeted integration strategy; FIG. 5B. Screening of single cell clones by junction PCR (upper panel: 5'end junction PCR using F1+R1 primers. 74 is the selected clone with insert for further characterization and 67 is a negative clone without insert; lower panel: 3' end junction PCR); FIG. 5C. Sequences of 5'end and 3'end of the insert in clone 74.

Neural stem cells are immunostaining with NSC-specific biomarkers sox-1 (red, staining nuclei) and nestin (green, staining cytoplasm). Functional neurons are immunostaining with neuron-specific biomarker Tujl (red) and nuclear staining dye Dapi (blue).

Figure 7:
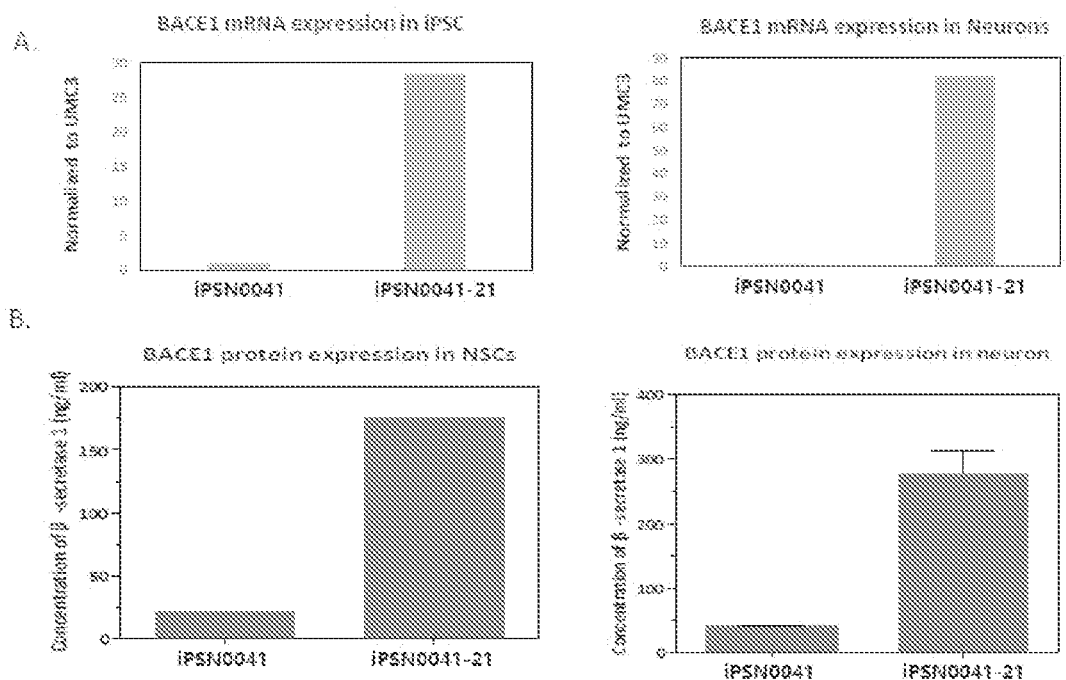

FIGS. 7A-7B. Over-expression of BACE1 gene in iPSN0041-21 in comparison with iPSN0041, showing that iPSN0041-21 has significantly higher expression of BACE1 gene at RNA and protein levels compared to those of the parental line iPSN0041. FIG. 7A. mRNA expression in hiPSC and in neurons derived from hiPSC between iPSN0041-21 and iPSN0041; FIG. 7B. BACE1 protein expression in neural stem cells and neurons derived from the hiPSC line.

Figure 8:
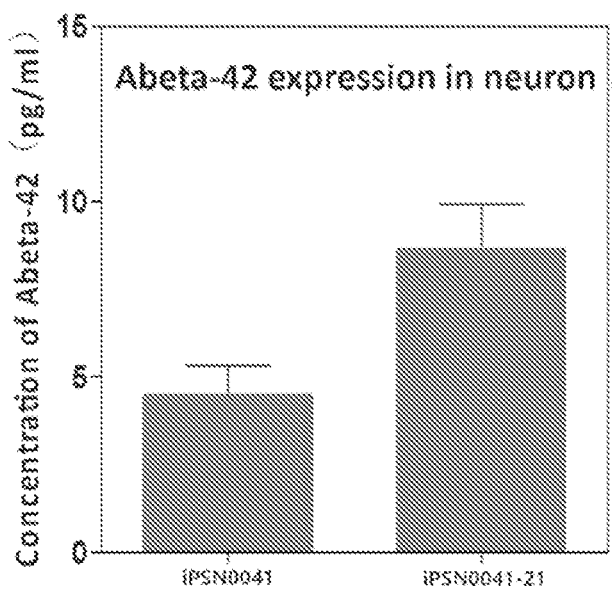
Figure 8:
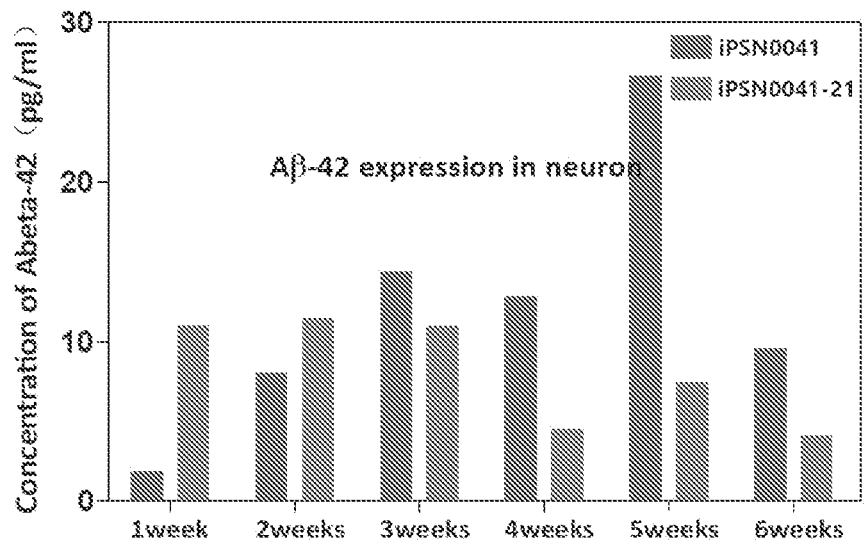

FIGS. 8A-8B. Over-expression of Abeta-42 peptides in iPSN0041-21 in comparison with iPSN0041. FIG. 8A. Abeta-42 concentration in hiPSC-derived neurons, showing that neurons derived from iPSN0041-21 have higher Abeta-42 concentration than that from iPSN0041; FIG. 8B. Time course study of Abeta-42 expression between iPSN0041-21 and iPSN0041, showing the different expression patterns.

Figure 9:
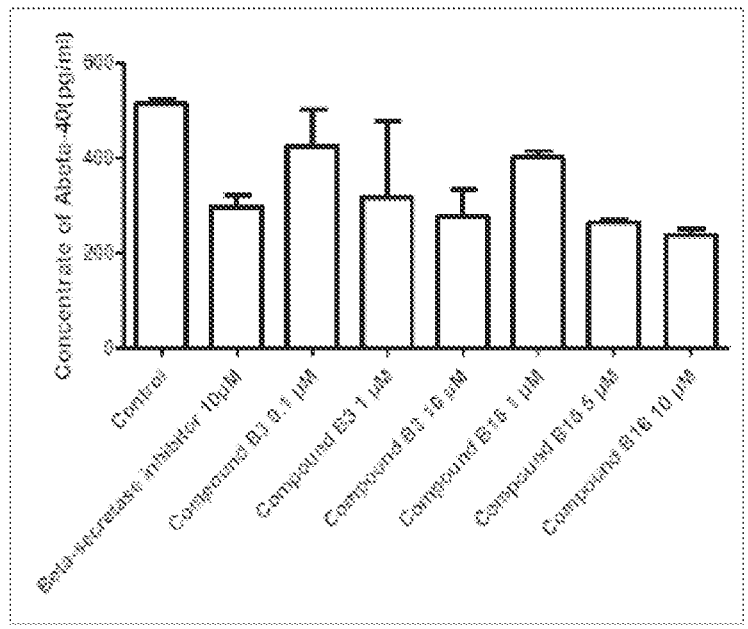
Figure 9:
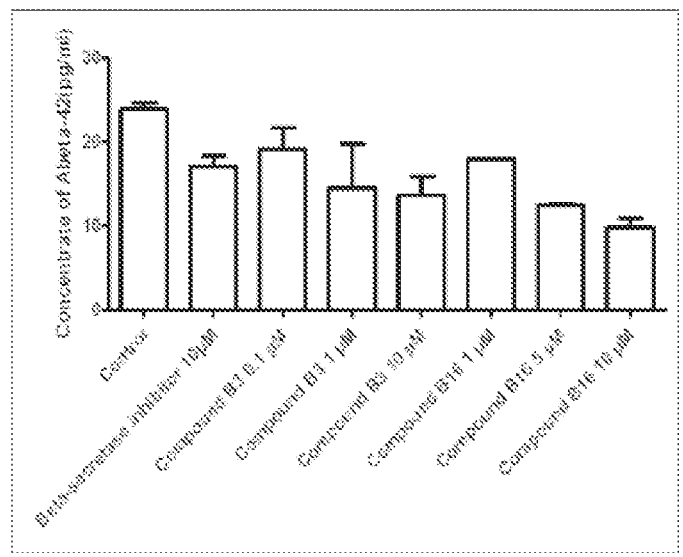
Figure 9:
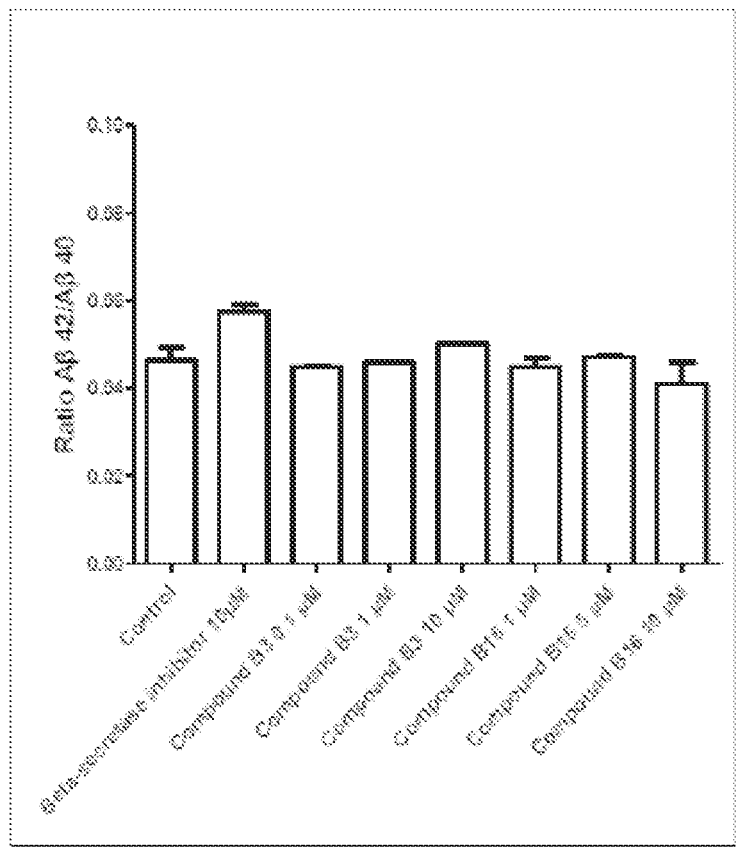

FIGS. 9A-9B. Example of drug screening using iPSN0041-21, showing that two small molecule compounds not being reported before, B3 and B16, reduce production of both Abeta-40 and Abeta-42 peptides in hiPSC-derived neurons, but not affect the Abeta-42/40 ratio. A known beta-secretase inhibitor (10 uM) is used as the positive control. Data are from three biological repeats. FIG. 9A. Reduction of B3 and B16 on Abeta-40 production; FIG. 9B. Reduction of B3 and B16 on Abeta-42 production; and FIG. 9C. Abeta-42 vs. Abeta-40 ratio.

DETAILED DESCRIPTION

All technical and scientific terms used herein have the same meaning as is commonly understood by one of ordinary skill in the art unless defined otherwise. For example, for terms in the biological field provided herein, practitioners are particularly directed to Sambrook et al., Molecular Cloning: A Laboratory Manual, 2$^{nd}$ ed., Cold Spring Harbor Press, Plainsview, N.Y. (1989); and Ausubel et al., Current Protocols in Molecular Biology (Supplement 47), John Wiley & Sons, New York (1999). Those terms should not be construed to have a scope less than understood by a person of ordinary skill in the art.

The term "comprising" is used in the present description and claims, it does not exclude other elements or steps. Where an indefinite or definite article is used when referring to a singular noun e.g. "a" or "an", "the", this includes a plural of that noun unless something else is specifically stated.

"AD-related gene" indicates any gene associated with the onset of Alzheimer's disease (AD). Although the cause of Alzheimer's disease is poorly understood, about 70% of the risk is believed to be genetic with many genes usually involved, for example, mutant genes encoding amyloid precursor protein (APP) and presenilins (PS) 1 and 2. The mutations in APP gene result in abnormal APP protein that is preferentially cleaved by beta-secretase to produce more Abeta peptides; whereas mutations in PS genes leads to preferentially production of Abeta42 peptide (Abeta-42 peptide), the constituent of amyloid plaques. Although there is no mutation in the gene encoding beta-secretase was found in either FAD or SAD patients, it is clear that elevated BACE1 expression results in elevated expression of Abeta peptides and thus increases the level of Abeta-42 peptides in AD patients. These genes, together with other genes found or will be found closely related to the onset of AD, are collectively denoted as AD-related gene in the present invention.

Mutant amyloid precursor protein (APP) or presenilins (PS) 1 and 2 gene herein indicates APP or PS1 or PS2 gene with mutations attributing to the onset of AD. The mutations of these genes may be naturally occurring in the AD patients or genetically created in vitro. When the term "BACE1 gene" is stated in the present invention, it encompassed not only the naturally occurring gene, but also its functional variants. The functional variants may be slightly different from the naturally occurring gene in amino acid sequence, for example, having at least 80%, preferably at least 90%, more preferably at least 95%, 96%, 97%, 98%, 99% homology with the amino acid sequence of the naturally occurring protein, but nevertheless, they still have the same function as the natural protein.

"Constitutive expression" means a gene that is transcribed continually compared to a facultative gene which is only transcribed as needed. "Overexpress" means an excessively high level of gene expression which produces a pronounced gene-related phenotype. As far as the present invention, the AD-related gene integrated into hiPSC is constitutively overexpressed in the hiPSC and leads to the appearance of phenotype of AD in the process of amyloid precursor protein.

"Phenotype of AD" in the present invention is related to the phenotype in the process of amyloid precursor protein induced by the integration of AD-related gene and constitutive overexpression of the integrated AD-related gene, including but not limited to increased beta-secretase level, amyloid beta peptide, Abeta-42 concentration and/or Abeta-42/Abeta-40.

In the present invention, the AD-related gene is integrated into hiPSC for constitutively overexpressing the AD-related gene to generate AD phenotype. The integration is carried out preferably by site-specific manner, most preferably, by using a sequence homologous to safe harbor site, i.e., human AAVS1 site. Being "homologous" is required to achieve homologous recombination so that the foreign gene can be integrated into the target site. A skilled person in the art, based on common knowledge, knows how to design a sequence homologous to the sequence at the target integration site to achieve the purpose of homologous recombination at the human AAVS1 site. Therefore, for such sequence, the embodiments encompassed by the present invention include but not limit to the exemplified.

Vectors

The cellular AD model of the present invention can be produced using genetic recombinant methods to introduce AD-related gene to the hiPSC derived from a non-diseased person. For recombinant production of the cellular model of AD, nucleic acids encoding the AD-related proteins, for example, mutant APP or PS protein, or BACE1 enzyme, is isolated and inserted into a replicable vector for further cloning (amplification of the DNA) or for expression. DNA encoding said proteins may be readily isolated and sequenced using conventional procedures in the art.

Many vectors are available for further arrangement for the purpose of the present invention. The components in the vectors generally include, but are not limited to, one or more of the following: an origin of replication, one or more marker genes, one or more report genes, an enhancer element, a promoter, and a transcription termination sequence.

Origin of Replication

Both expression and cloning vectors contain a nucleic acid sequence that enables the vector to replicate in the selected host cell.

Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2p plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, uromycine, kanamycine, and geneticine (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, uromycine, kanamycine, and geneticine and hygromycin.

Another example of suitable selectable markers for mammalian cells are those that enable the identification of cells competent to take up antibody encoding nucleic acid, such as DHFR, glutamine synthetase (GS), thymidine kinase, metallothionein-1 and -11, preferably primate metallothionein genes, adenosine 20 deaminase, ornithine decarboxylase, etc.

For example, cells transformed with the DHFR gene are identified by culturing the transformants in a culture medium containing methotrexate (Mtx), a competitive antagonist of DHFR. Under these conditions, the DHFR gene is amplified along with any other co-transformed nucleic acid.

Alternatively, cells transformed with the GS gene are identified by culturing the transformants in a culture medium containing L-methionine sulfoximine (Msx), an inhibitor of GS. Under these conditions, the GS gene is amplified along with any other co-transformed nucleic acid. The GS selection/amplification system may be used in combination with the DHFR selection/amplification system described above.

Report Gene Component

A reporter gene (often simply reporter) is a gene that researchers attach to a regulatory sequence of another gene of interest in organisms. Certain genes are chosen as reporters because the characteristics they confer on organisms expressing them are easily identified and measured, or because they are selectable markers. Reporter genes are often used as an indication of whether a certain gene has been taken up by or expressed in the cell or organism population.

To introduce a reporter gene into an organism, scientists place the reporter gene and the gene of interest in the same DNA construct to be inserted into the cell or organism. Commonly used reporter genes that induce visually identifiable characteristics usually involve fluorescent and luminescent proteins. Examples include the gene that encodes jellyfish green fluorescent protein (GFP), which causes cells that express it to glow green under blue light, and the red fluorescent protein from the gene dsRed.

Promoter Component

Expression and cloning vectors generally contain a promoter that is recognized by the host cell and is operably linked to nucleic acid encoding the interested protein.

Promoter sequences are known for eukaryotes. Virtually all eukaryotic genes have an AT-rich region located approximately to bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the polyA tail to the 3' end of the coding sequence. All of these sequences are suitably inserted into eukaryotic expression vectors.

The AD disease-causing protein transcription from vectors in hiPSC can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), or from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human p-interferon cDNA in mouse cells under the control of a thymidine kinase 5 promoter from herpes simplex virus. Alternatively, the Rous Sarcoma Virus long terminal repeat can be used as the promoter.

The CAG promoter is a strong synthetic promoter frequently used to drive high levels of gene expression in mammalian expression vectors (ref 37-38). It was constructed from the following sequences:

(C) the cytomegalovirus (CMV) early enhancer element,
(A) the promoter, the first exon and the first intron of chicken beta-actin gene,
(G) the splice acceptor of the rabbit beta-globin gene The resulting synthetic element was used in the pCAGGS expression vector.

Although the whole construct is commonly referred to as the "CAG promoter", it is not a promoter in a strict sense, as it includes a part of the transcribed sequence and an intron) and enhancer elements. In addition to the CMV immediate early enhancer, the intron of the chicken beta actin gene contains an enhancer element, which is highly conserved among vertebrates. The 3' part of the promoter has high GC content and is thus refractory to PCR amplification.

The PGK-1 gene encodes the housekeeping enzyme, 3-phosphoglycerate kinase, and is ubiquitously expressed. This gene resides on the X chromosome in mammals and is always expressed except where it is silenced along with most other genes on the inactive X chromosome of female somatic cells or male germ cells. The PGK-1 promoter is in a region rich in nucleotides G and C. This promoter can efficiently drive high levels of expression of reporter genes such as *E. coli* lacZ and neo. The 120 bp upstream of the transcription start site functions as a core promoter. Upstream of this is a 320 bp region which enhances transcription from the core promoter in an orientation and position independent fashion. This 320 bp region does not enhance transcription from the core promoter of the SV40 early region. Nuclear proteins bind to this 320 bp fragment although the restricted regions to which binding can be demonstrated with gel mobility shift assays suggests that the activity of the enhancer may be mediated by factors which bind at multiple sites each with low affinity (ref 39).

Enhancer Element Component

Transcription of a DNA encoding the interested protein by higher eukaryotes is often increased by inserting an enhancer sequence into the vector. Many enhancer sequences are now known from mammalian genes (globin, elastase, albumin, a-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody-encoding sequence, but is preferably located at a site 5' from the promoter.

Transcription Termination Component

Expression vectors used in eukaryotic host cells, for example human cells, will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the interested protein.

In one embodiment, the vector of the present invention is designed for targeted integration of genes associated with Alzheimer's disease (AD)-related genes into human pluripotent stem cell (hiPSC) with high efficiency. Therefore, the vector is also arranged to contain a sequence for site-specific integration.

The insertion of genes at known locations by enzymes with target recognition capacity is a kind of technology targeting genome edition, which enables researchers to delete, insert, or modify any genes or DNA segments at genome level with high efficiency and precision (ref 40-42). Such technology also includes recently wide-used CRISPRcas9 gene editing technique disclosed in for example, U.S. Pat. Nos. 8,697,359, 8,771,945, 8,795,965. In certain embodiments of the present invention, the AD-related genes are integrated specifically to the safe harbor site, i.e., AAVS1 site, by CRISPRcas9 gene editing technique.

AAVS1 site is a natural AAV integration site on human chromosome 19. This region (AAVS1) has characteristics that make it an ideal target for transgenesis.

In one specific embodiment of the present invention, the vector comprises a drug selection marker gene controlled by a first promoter, an AD-related gene linked with a reporter gene controlled by a second promoter, and sequences homologous to those at human AAVS1 site.

Figure 4:
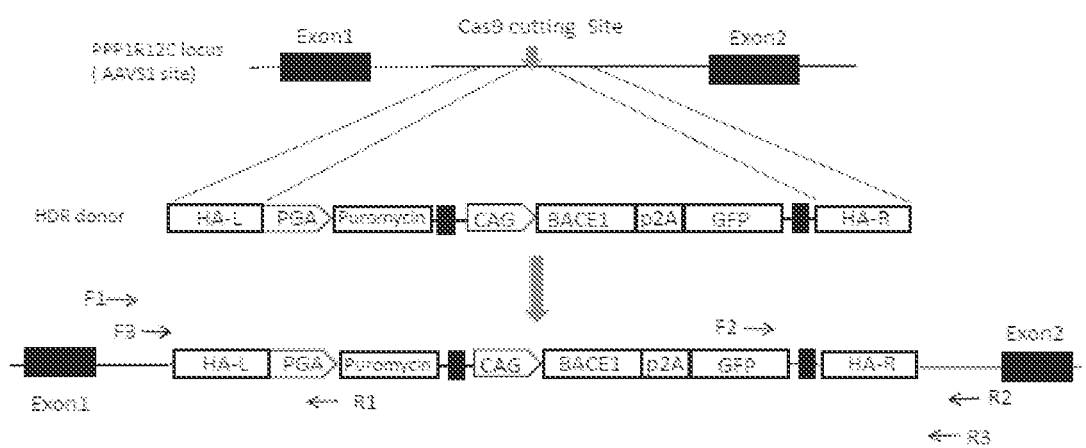
FIGS. 4A-4C. Targeted integration of BACE1 gene into AAVS1 site. AAVS1 site is located in the intron region of Exon 1 and Exon 2 of PPP1R12C locus. F1, F2, F3, R1, R2, and R3 are primers used for verification of insertion by junction PCR.
Figure 4:
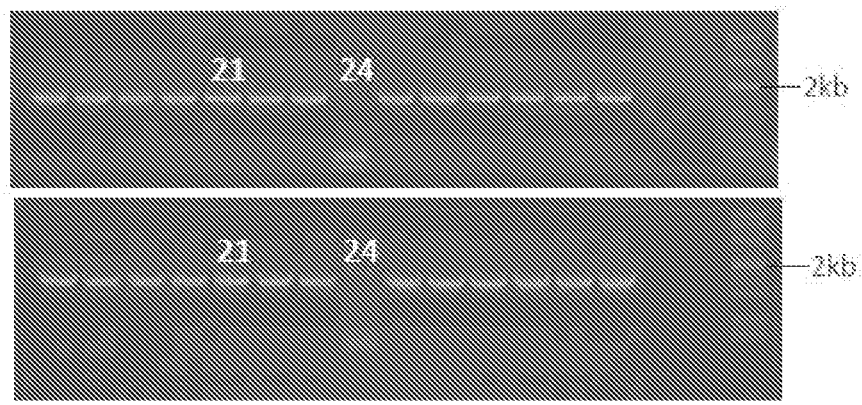
Figure 4:
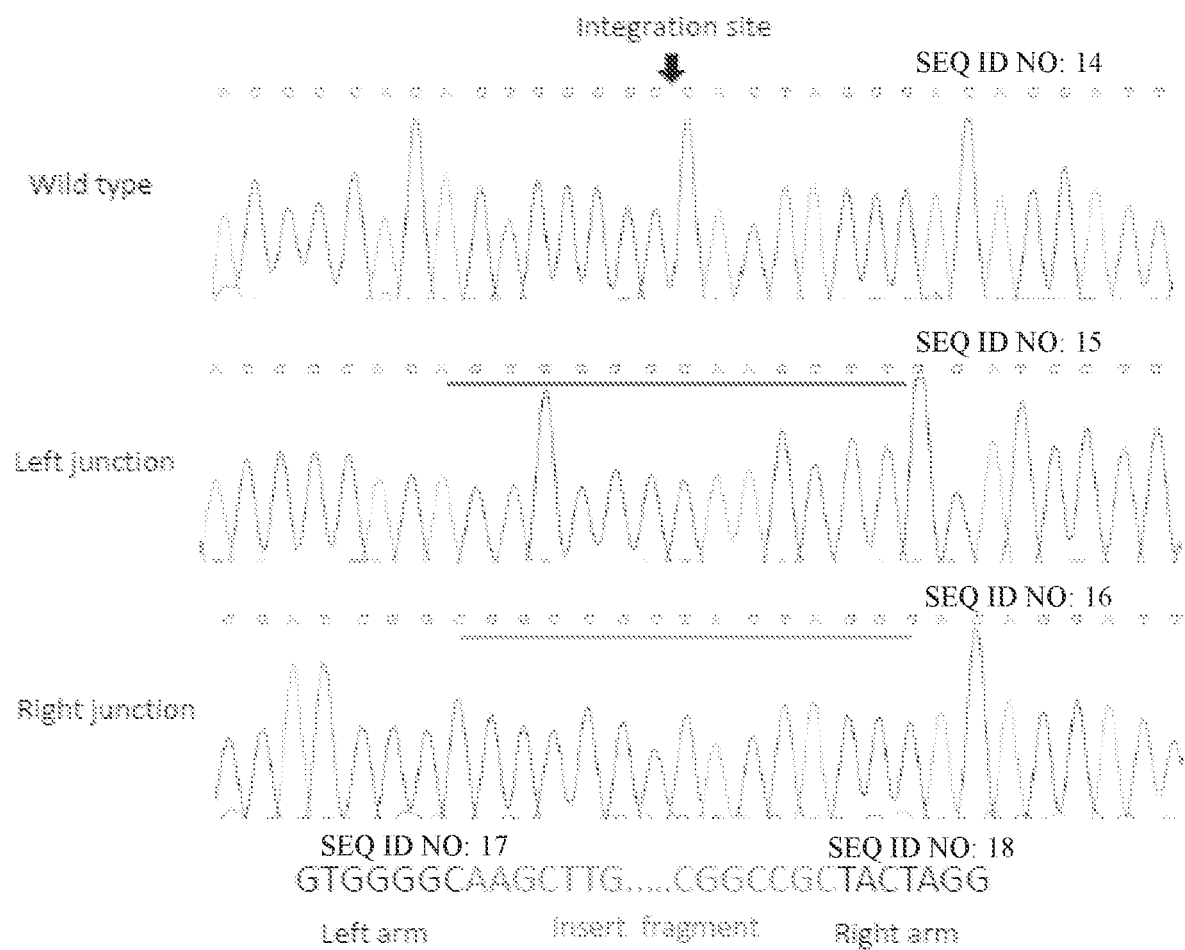

In one specific embodiment of the present invention, the donor vector backbone contains a left arm for targeted integration (HA-L), PGK-1 promoter, a puromycine gene, a CAG promoter, a GFP reporter gene and a right arm for targeted integration (HA-RL) in a cis arrangement (FIG. 4A).

As used herein, the left arm for targeted integration (HA-L) comprises the sequence:

```
                                        (SEQ ID NO. 1)
TGCTTTCTCTGACCAGCATTCTCTCCCCTGGGCCTGTGCCGCTTTCTGTC

TGCAGCTTGTGGCCTGGGTCACCTCTACGGCTGGCCCAGATCCTTCCCTG

CCGCCTCCTTCAGGTTCCGTCTTCCTCCACTCCCTCTTCCCCTTGCTCTC

TGCTGTGTTGCTGCCCAAGGATGCTCTTTCCGGAGCACTTCCTTCTCGGC

GCTGCACCACGTGATGTCCTCTGAGCGGATCCTCCCCGTGTCTGGGTCCT

CTCCGGGCATCTCTCCTCCCTCACCCAACCCCATGCCGTCTTCACTCGCT

GGGTTCCCTTTTCCTTCTCCTTCTGGGGCCTGTGCCATCTCTCGTTTCTT

AGGATGGCCTTCTCCGACGGATGTCTCCCTTGCGTCCCGCCTCCCCTTCT

TGTAGGCCTGCATCATCACCGTTTTTCTGGACAACCCCAAAGTACCCCGT

CTCCCTGGCTTTAGCCACCTCTCCATCCTCTTGCTTTCTTTGCCTGGACA

CCCCGTTCTCCTGTGGATTCGGGTCACCTCTCACTCCTTTCATTTGGGCA

GCTCCCCTACCCCCCTTACCTCTCTAGTCTGTGCTAGCTCTTCCAGCCCC

CTGTCATGGCATCTTCCAGGGGTCCGAGAGCTCAGCTAGTCTTCTTCCTC

CAACCCGGGCCCCTATGTCCACTTCAGGACAGCATGTTTGCTGCCTCCAG

GGATCCTGTGTCCCCGAGCTGGGACCACCTTATATTCCCAGGGCCGGTTA

ATGTGGCTCTGGTTCTGGGTACTTTTATCTGTCCCCTCCACCCCACAGTG

GGGC.
```

The PGK-puromycin cassette comprises the sequence:

```
                                        (SEQ ID NO. 2)
ATAACTTCGTATAATGTATGCTATACGAAGTTATTACCGGGTAGGGGAGG

CGCTTTTCCCAAGGCAGTCTGGAGCATGCGCTTTAGCAGCCCCGCTGGGC

ACTTGGCGCTACACAAGTGGCCTCTGGCCTCGCACACATTCCACATCCCC

CGGTAGGCGCCAACCGGCTCCGTTCTTTGGTGGCCCCTTCGCGCCACCTT

CTACTCCTCCCCTAGTCAGGAAGTTCCCCCCCGCCCCGCAGCTCGCGTCG

TGCAGGACGTGACAAATGGAAGTAGCACGTCTCACTAGTCTCGTGCAGAT

GGACAGCACCGCTGAGCAATGGAAGCGGGTAGGCCTTTGGGGCAGCGGCC

AATAGCAGCTTTGCTCCTTCGCTTTCTGGGCTCAGAGGCTGGGAAGGGGT

GGGTCCGGGGGCGGGCTCAGGGGCGGGCTCAGGGGCGGGGCGGGCGCCCG

AAGGTCCTCCGGAGGCCCGGCATTCTGCACGCTTCAAAAGCGCACGTCTG

CCGCGCTGTTCTCCTCTTCCTCATCTCCGGGCCTTTCGGAATTCATGACC

GAGTACAAGCCCACGGTGCGCCTCGCCACCCGCGACGACGTCCCCCGGGC

CGTACGCACCCTCGCCGCCGCGTTCGCCGACTACCCCGCCACGCGCCACA

CCGTCGACCCGGACCGCCACATCGAGCGGGTCACCGAGCTGCAAGAACTC

TTCCTCACGCGCGTCGGGCTCGACATCGGCAAGGTGTGGGTCGCGGACGA

CGGCGCCGCGGTGGCGGTCTGGACCACGCCGGAGAGCGTCGAAGCGGGGG

CGGTGTTCGCCGAGATCGGCCCGCGCATGGCCGAGTTGAGCGGTTCCCGG
```

CTGGCCGCGCAGCAACAGATGGAAGGCCTCCTGGCGCCGCACCGGCCCAA

GGAGCCCGCGTGGTTCCTGGCCACCGTCGGCGTCTCGCCCGACCACCAGG

GCAAGGGTCTGGGCAGCGCCGTCGTGCTCCCCGGAGTGGAGGCGGCCGAG

CGCGCCGGGGTGCCCGCCTTCCTGGAGACCTCCGCGCCCCGCAACCTCCC

CTTCTACGAGCGGCTCGGCTTCACCGTCACCGCCGACGTCGAGGTGCCCG

AAGGACCGCGCACCTGGTGCATGACCCGCAAGCCCGGTGCCTGATAGAAC

TTGTTTATTGCAGCTTATAATGGTTACAAATAAAGCAATAGCATCACAAA

TTTCACAAATAAAGCATTTTTTTCACTGCATTCTAGTTGTGGTTTGTCCA

AACTCATCAATGTATCTTATCATGTCTGATAACTTCGTATAATGTATGCT

ATACGAAGTTAT.

The CAG promoter comprises the sequence:

(SEQ ID NO. 3)
ATTGATTATTGACTAGTTATTAATAGTAATCAATTACGGGGTCATTAGTT

CATAGCCCATATATGGAGTTCCGCGTTACATAACTTACGGTAAATGGCCC

GCCTGGCTGACCGCCCAACGACCCCCGCCCATTGACGTCAATAATGACGT

ATGTTCCCATAGTAACGCCAATAGGGACTTTCCATTGACGTCAATGGGTG

GAGTATTTACGGTAAACTGCCCACTTGGCAGTACATCAAGTGTATCATAT

GCCAAGTACGCCCCCTATTGACGTCAATGACGGTAAATGGCCCGCCTGGC

ATTATGCCCAGTACATGACCTTATGGGACTTTCCTACTTGGCAGTACATC

TACGTATTAGTCATCGCTATTACCATGGTCGAGGTGAGCCCCACGTTCTG

CTTCACTCTCCCCATCTCCCCCCCCTCCCCACCCCCAATTTTGTATTTAT

TTATTTTTTAATTATTTTGTGCAGCGATGGGGGCGGGGGGGGGGGGGGGC

GCGCGCCAGGCGGGGCGGGGCGGGGCGAGGGGCGGGGCGGGGCGAGGCGG

AGAGGTGCGGCGGCAGCCAATCAGAGCGGCGCGCTCCGAAAGTTTCCTTT

TATGGCGAGGCGGCGGCGGCGGCGCCCTATAAAAAGCGAAGCGCGCGGC

GGGCGGGAGTCGCTGCGCGCTGCCTTCGCCCCGTGCCCCGCTCCGCCGCC

GCCTCGCGCCGCCCGCCCCGGCTCTGACTGACCGCGTTACTCCCACAGGT

GAGCGGGCGGGACGGCCCTTCTCCTCCGGGCTGTAATTAGCGCTTGGTTT

AATGACGGCTTGTTTCTTTTCTGTGGCTGCGTGAAAGCCTTGAGGGGCTC

CGGGAGGGCCCTTTGTGCGGGGGGAGCGGCTCGGGGGGTGCGTGCGTGTG

TGTGTGCGTGGGGAGCGCCGCGTGCGGCTCCGCGCTGCCCGGCGGCTGTG

AGCGCTGCGGGCGCGGCGCGGGGCTTTGTGCGCTCCGCAGTGTGCGCGAG

GGGAGCGCGGCCGGGGCGGTGCCCCGCGGTGCGGGGGGCTGCGAGGGG

AACAAAGGCTGCGTGCGGGGTGTGTGCGTGGGGGGGTGAGCAGGGGGTGT

GGGCGCGTCGGTCGGGCTGCAACCCCCCCTGCACCCCCCTCCCCGAGTTG

CTGAGCACGCCCGGCTTCGGGTGCGGGGCTCCGTACGGGGCGTGGCGCG

GGGCTCGCCGTGCCGGGCGGGGGTGGCGGCAGGTGGGGGTGCCGGGCGG

GGCGGGGCCGCCTCGGGCCGGGGAGGGCTCGGGGGAGGGGCGCGGCGGCC

CCCGGAGCGCCGGCGGCTGTCGAGGCGCGGCGAGTCGCAGCCATTGCCTT

TTATGGTAATCGTGCGAGAGGGCGCAGGGACTTCCTTTGTCCCAAATCTG

TGTGGAGCCGAAATCTGGGAGGCGCCGCCGCACCCCCTCTAGCGGGCGCG

GGGCGAAGCGGTGCGGCGCCGGCAGGAAGGAAATGGGCGGGGAGGGCCTT

CGTGCGTCGCCGCGCCGCCGTCCCCTTCTCCCTCTCCAGCCTCGGGGCTG

TCCGCGGGGGGCGGCTGCCTTCGGGGGGACGGGGCAGGGCGGGGTTCG

GCTTCTGGCGTGTGACCGGCGGCTCTAGAGCCTCTGCTAACCATGTTCAT

GCCTTCTTCTTTTTCCTACAGCTCCTGGGCAACGTGCTGGTTATTGTGCT

GTCTCATCATTTTGGCAAAGAATTCCTCGACCTCGAG.

The GFP reporter gene comprises the sequence:

(SEQ ID NO. 4)
AGATCTGGCAGCGGAGAGGGCAGAGGAAGTCTTCTAACATGCGGTGACGT

GGAGGAGAATCCCGGCCCTAGGTTCGAAATGGTGAGCAAGGGCGAGGAGC

TGTTCACCGGGGTGGTGCCCATCCTGGTCGAGCTGGACGGCGACGTAAAC

GGCCACAAGTTCAGCGTGTCCGGCGAGGGCGAGGGCGATGCCACCTACGG

CAAGCTGACCCTGAAGTTCATCTGCACCACCGGCAAGCTGCCCGTGCCCT

GGCCCACCCTCGTGACCACCTTGACCTACGGCGTGCAGTGCTTCGCCCGC

TACCCCGACCACATGAAGCAGCACGACTTCTTCAAGTCCGCCATGCCCGA

AGGCTACGTCCAGGAGCGCACCATCTTCTTCAAGGACGACGGCAACTACA

AGACCCGCGCCGAGGTGAAGTTCGAGGGCGACACCCTGGTGAACCGCATC

GAGCTGAAGGGCATCGACTTCAAGGAGGACGGCAACATCCTGGGGCACAA

GCTGGAGTACAACTACAACAGCCACAAGGTCTATATCACCGCCGACAAGC

AGAAGAACGGCATCAAGGTGAACTTCAAGACCCGCCACAACATCGAGGAC

GGCAGCGTGCAGCTCGCCGACCACTACCAGCAGAACACCCCCATCGGCGA

CGGCCCCGTGCTGCTGCCCGACAACCACTACCTGAGCACCCAGTCCGCCC

TGAGCAAAGACCCCAACGAGAAGCGCGATCACATGGTCCTGCTGGAGTTC

GTGACCGCCGCCGGGATCACTCTCGGCATGGACGAGCTGTACAAGTGA.

The right arm for targeted integration (HA-RL) comprises the sequence (SEQ ID NO.5):

TACTAGGGACAGGATTGGTGACAGAAAAGCCCCATCCTTAGGCCTCCTCC

TTCCTAGTCTCCTGATATTGGGTCTAACCCCCACCTCCTGTTAGGCAGAT

TCCTTATCTGGTGACACACCCCCATTTCCTGGAGCCATCTCTCTCCTTGC

CAGAACCTCTAAGGTTTGCTTACGATGGAGCCAGAGAGGATCCTGGGAGG

GAGAGCTTGGCAGGGGGTGGGAGGGAAGGGGGGGATGCGTGACCTGCCCG

GTTCTCAGTGGCCACCCTGCGCTACCCTCTCCCAGAACCTGAGCTGCTCT

GACGCGGCTGTCTGGTGCGTTTCACTGATCCTGGTGCTGCAGCTTCCTTA

CACTTCCCAAGAGGAGAAGCAGTTTGGAAAAACAAAATCAGAATAAGTTG

GTCCTGAGTTCTAACTTTGGCTCTTCACCTTTCTAGTCCCCAATTTATAT

TGTTCCTCCGTGCGTCAGTTTTACCTGTGAGATAAGGCCAGTAGCCAGCC

CCGTCCTGGCAGGGCTGTGGTGAGGAGGGGGGTGTCCGTGTGGAAAACTC

CCTTTGTGAGAATGGTGCGTCCTAGGTGTTCACCAGGTCGTGGCCGCCTC

TACTCCCTTTCTCTTTCTCCATCCTTCTTTCCTTAAAGAGTCCCCAGTGC

-continued
TATCTGGGACATATTCCTCCGCCCAGAGCAGGGTCCCGCTTCCCTAAGGC

CCTGCTCTGGGCTTCTGGGTTTGAGTCCTTGGCAAGCCCAGGAGAGGCGC

TCAGGCTTCCCTGTCCCCCTTCCTCGTCCACCATCTCATGCCCCTGGCTC

TCCTGCCCCTTCCCTACAGGGGTTCCTGGCTCTGCTCT.

In another specific embodiment, the donor vector comprises a BACE1 gene that is inserted into the vector backbone at the BglII and XhoI site (FIG. 5B); cDNA sequence for BACE1 gene is disclosed in Genbank under locus NM_138973.3 (*Homo sapiens* beta-secretase 1, transcript variant d, mRNA). As used herein, "BACE1" denotes a transmembrane protease encoded by BACE1 gene. BACE1 catalyzes the first step in the formation of amyloid beta peptide from amyloid precursor protein. Amyloid beta peptides are the main constituent of amyloid beta plaques, which accumulate in the brains of human Alzheimer's disease patients.

The DNA sequence of BACE1 gene in the donor vector is described as:

(SEQ ID NO. 6)
ATGGCCCAAGCCCTGCCCTGGCTCCTGCTGTGGATGGGCGCGGGAGTGCT

GCCTGCCCACGGCACCCAGCACGGCATCCGGCTGCCCCTGCGCAGCGGCC

TGGGGGGCGCCCCCCTGGGGCTGCGGCTGCCCCGGGAGACCGACGAAGAG

CCCGAGGAGCCCGGCCGGAGGGGCAGCTTTGTGGAGATGGTGGACAACCT

GAGGGGCAAGTCGGGGCAGGGCTACTACGTGGAGATGACCGTGGGCAGCC

CCCCGCAGACGCTCAACATCCTGGTGGATACAGGCAGCAGTAACTTTGCA

GTGGGTGCTGCCCCCCACCCCTTCCTGCATCGCTACTACCAGAGGCAGCT

GTCCAGCACATACCGGGACCTCCGGAAGGGTGTGTATGTGCCCTACACCC

AGGGCAAGTGGGAAGGGGAGCTGGGCACCGACCTGCTTTGTGGTGCTGGC

TTCCCCCTCAACCAGTCTGAAGTGCTGGCCTCTGTCGGAGGGAGCATGAT

CATTGGAGGTATCGACCACTCGCTGTACACAGGCAGTCTCTGGTATACAC

CCATCCGGCGGGAGTGGTATTATGAGGTGATCATTGTGCGGGTGGAGATC

AATGGACAGGATCTGAAAATGGACTGCAAGGAGTACAACTATGACAAGAG

CATTGTGGACAGTGGCACCACCAACCTTCGTTTGCCCAAGAAAGTGTTTG

AAGCTGCAGTCAAATCCATCAAGGCAGCCTCCTCCACGGAGAAGTTCCCT

GATGGTTTCTGGCTAGGAGAGCAGCTGGTGTGCTGGCAAGCAGGCACCAC

CCCTTGGAACATTTTCCCAGTCATCTCACTCTACCTAATGGGTGAGGTTA

CCAACCAGTCCTTCCGCATCACCATCCTTCCGCAGCAATACCTGCGGCCA

GTGGAAGATGTGGCCACGTCCCAAGACGACTGTTACAAGTTTGCCATCTC

ACAGTCATCCACGGGCACTGTTATGGGAGCTGTTATCATGGAGGGCTTCT

ACGTTGTCTTTGATCGGGCCCGAAAACGAATTGGCTTTGCTGTCAGCGCT

TGCCATGTGCACGATGAGTTCAGGACGGCAGCGGTGGAAGGCCCTTTTGT

CACCTTGGACATGGAAGACTGTGGCTACAACATTCCACAGACAGATGAGT

CAACCCTCATGACCATAGCCTATGTCATGGCTGCCATCTGCGCCCTCTTC

ATGCTGCCACTCTGCCTCATGGTGTGTCAGTGGCGCTGCCTCCGCTGCCT

GCGCCAGCAGCATGATGACTTTGCTGATGACATCTCCCTGCTGA.

And the protein sequence (SEQ ID NO.7) of BACE1 is described as:

MAQALPWLLLWMGAGVLPAHGTQHGIRLPLRSGLGGAPLGLRLPRETDEE

PEEPGRRGSFVEMVDNLRGKSGQGYYVEMTVGSPPQTLNILVDTGSSNFA

VGAAPHPFLHRYYQRQLSSTYRDLRKGVYVPYTQGKWEGELGTDLLCGAG

FPLNQSEVLASVGGSMIIGGIDHSLYTGSLWYTPIRREWYYEVIIVRVEI

NGQDLKMDCKEYNYDKSIVDSGTTNLRLPKKVFEAAVKSIKAASSTEKFP

DGFWLGEQLVCWQAGTTPWNIFPVISLYLMGEVTNQSFRITILPQQYLRP

VEDVATSQDDCYKFAISQSSTGTVMGAVIMEGFYVVFDRARKRIGFAVSA

CHVHDEFRTAVEGPFVTLDMEDCGYNIPQTDESTLMTIAYVMAAICALFM

LPLCLMVCQWRCLRCLRQQHDDFADDISLLK.

In another specific embodiment, the donor vector comprises PS1dE9 gene that is inserted into the vector backbone at the BglII and XhoI site (FIG. 4B). PS1dE9 is a mutant of PS1 gene with Exon 9 of PS1 gene being deleted. As used herein, the term "PS1" denotes a protein encoded by the presenilin 1 gene. cDNA sequence for PS1 gene is disclosed in Genbank under locus NM_000021.3 (*Homo sapiens*, presenilin 1, transcript variant 1, mRNA). Presenilin 1 is one of the four core proteins in presenilin complex, which mediate the regulated proteolytic events of several proteins in the cell, including gamma secretase. The term "PS1dE9" denotes a mutant gene of PS1, which causes abnormal Gamma-secretase cleavage that is favorable for production of Abeta-42 peptides and thus results in early onset of Alzheimer's disease.

The DNA sequence of PS1dE9 in the donor vector is described below (highlighted is the deleted sequence):

(SEQ ID NO. 8)
ATGACAGAGTTACCTGCACCGTTGTCCTACTTCCAGAATGCACAGATGTC

TGAGGACAACCACCTGAGCAATACTGTACGTAGCCAGAATGACAATAGAG

AACGGCAGGAGCACAACGACAGACGGAGCCTTGGCCACCCTGAGCCATTA

TCTAATGGACGACCCCAGGGTAACTCCCGGCAGGTGGTGGAGCAAGATGA

GGAAGAAGATGAGGAGCTGACATTGAAATATGGCGCCAAGCATGTGATCA

TGCTCTTTGTCCCTGTGACTCTCTGCATGGTGGTGGTCGTGGCTACCATT

AAGTCAGTCAGCTTTTATACCCGGAAGGATGGGCAGCTAATCTATACCCC

ATTCACAGAAGATACCGAGACTGTGGGCCAGAGAGCCCTGCACTCAATTC

TGAATGCTGCCATCATGATCAGTGTCATTGTTGTCATGACTATCCTCCTG

GTGGTTCTGTATAAATACAGGTGCTATAAGGTCATCCATGCCTGGCTTAT

TATATCATCTCTATTGTTGCTGTTCTTTTTTTCATTCATTTACTTGGGGG

AAGTGTTTAAAACCTATAACGTTGCTGTGGACTACATTACTGTTGCACTC

CTGATCTGGAATTTTGGTGTGGTGGGAATGATTTCCATTCACTGGAAAGG

TCCACTTCGACTCCAGCAGGCATATCTCATTATGATTAGTGCCCTCATGG

CCCTGGTGTTTATCAAGTACCTCCCTGAATGGACTGCGTGGCTCATCTTG

GCTGTGATTTCAGTATATGATTTAGTGGCTGTTTTGTGTCCGAAAGGTCC

ACTTCGTATGCTGGTTGAAACAGCTCAGGAGAGAAATGAAACGCTTTTTC

-continued
```
CAGCTCTCATTTACTCCTGAAGAATGGTGTGGTTGGTGAATATGGGAGA

AGGAGACCCGGAAGCTCAAAGGAGATATCCAAAAATTGCAAGTATAATG

CAGAAAGCACAGAAAGGGAGTCACAAGACACTGTTGCAGAGAATGATGAT

GGCGGGTTCAGTGAGGAATGGGAAGCCCAGAGGGACAGTCATCTAGGGCC

TCATCGCTCTACACCTGAGTCACGAGCTGCTGTCCAGGAACTTTCCAGCA

GTATCCTCGCTGGTGAAGACCCAGAGGAAAGGGGAGTAAAACTTGGATTG

GGAGATTTCATTTTCTACAGTGTTCTGGTTGGTAAAGCCTCAGCAACAGC

CAGTGGAGACTGGAACACAACCATAGCCTGTTTCGTAGCCATATTAATTG

GTTTGTGCCTTACATTATTACTCCTTGCCATTTTCAAGAAAGCATTGCCA

GCTCTTCCAATCTCCATCACCTTTGGGCTTGTTTTCTACTTTGCCACAGA

TTATCTTGTACAGCCTTTTATGGACCAATTAGCATTCCATCAATTTTATA

TCTAG.
```

And the protein sequence of PS1dE9 is described below (highlighted is the miss-translated part due to deletion of Exon9):

(SEQ ID NO. 9)
```
MTELPAPLSYFQNAQMSEDNHLSNTVRSQNDNRERQEHNDRRSLGHPEPL

SNGRPQGNSRQVVEQDEEEDEELTLKYGAKHVIMLFVPVTLCMVVVVATI

KSVSFYTRKDGQLIYTPFTEDTETVGQRALHSILNAAIMISVIVVMTILL

VVLYKYRCYKVIHAWLIISSLLLLFFFSFIYLGEVFKTYNVAVDYITVAL

LIWNFGVVGMISIHWKGPLRLQQAYLIMISALMALVFIKYLPEWTAWLIL

AVISVYDLVAVLCPKGPLRMLVETAQERNETLFPALIYSSSIMQKAQKG

SHKTLLQRMMMAGSVRNGKPRGTVI*GLIALHLSHELLSRNFPAVSSLV

KTQRKGE*NLDWEISFSTVFWLVKPQQQPVETGTQP*PVS*PY*LVCAL

HYYSLPFSRKHCQLFQSPSPLGLFSTLPQIILYSLLWTN*HSINFISX.
```

In another embodiment of the present invention, the donor vector of the invention may comprise any functional variant of BACE1 and/or any variant of PS1 attributing to the onset of AD. The variants include, for instance, naturally-occurring variants due to allelic variations between individuals (e.g., polymorphisms), alternative splicing forms, etc. Variants are preferably substantially homologous to sequences according to the present invention, i.e., exhibit a nucleotide sequence identity of typically at least about 80%, preferably at least about 90%, more preferably at least about 95%, 96%, 97%, 98%, 99% with sequences of the present invention. Variants of the genes of the present invention also include nucleic acid sequences, which hybridize to a sequence as defined above (or a complementary strand thereof) under stringent hybridization conditions. Typical stringent hybridization conditions include temperatures above 42° C. and salinity of equal or less than 200 mM.

hiPSC Lines

In one embodiment the present disclosure relates to creation of an hiPSC line that has an AD-related gene integrated at a safe harbor site (AAVS1 site) by the method of the present invention. The hiPSC line created by the present invention constitutively over-expresses the integrated gene and displays increased beta-secretase level and/or Abeta-42 peptides compared to an isogenic control hiPSC line without gene integration.

In one specific embodiment, an hiPSC line made by the method of the present invention has an exogenous nucleic acid sequence integrated at AAVS1 site. The nucleic acid sequence comprises a PGK-1 promoter, a puromycin gene, a CAG promoter, a BACE1 gene, and a GFP gene and sequences that link different segments. The inserted nucleic acid sequence is described below (the underlined art is BACE1 gene):

(SEQ ID NO. 10)
```
ATAACTTCGTATAATGTATGCTATACGAAGTTATTACCGGGTAGGGGAGG

CGCTTTTCCCAAGGCAGTCTGGAGCATGCGCTTTAGCAGCCCCGCTGGGC

ACTTGGCGCTACACAAGTGGCCTCTGGCCTCGCACACATTCCACATCCCC

CGGTAGGCGCCAACCGGCTCCGTTCTTTGGTGGCCCCTTCGCGCCACCTT

CTACTCCTCCCCTAGTCAGGAAGTTCCCCCCCGCCCCGCAGCTCGCGTCG

TGCAGGACGTGACAAATGGAAGTAGCACGTCTCACTAGTCTCGTGCAGAT

GGACAGCACCGCTGAGCAATGGAAGCGGGTAGGCCTTTGGGGCAGCGGCC

AATAGCAGCTTTGCTCCTTCGCTTTCTGGGCTCAGAGGCTGGGAAGGGGT

GGGTCCGGGGCGGGCTCAGGGGCGGGCTCAGGGGCGGGCGGGCGCCCG

AAGGTCCTCCGGAGGCCCGGCATTCTGCACGCTTCAAAAGCGCACGTCTG

CCGCGCTGTTCTCCTCTTCCTCATCTCCGGGCCTTTCGGAATTCATGACC

GAGTACAAGCCCACGGTGCGCCTCGCCACCCGCGACGACGTCCCCCGGGC

CGTACGCACCCTCGCCGCCGCGTTCGCCGACTACCCCGCCACGCGCCACA

CCGTCGACCCGGACCGCCACATCGAGCGGGTCACCGAGCTGCAAGAACTC

TTCCTCACGCGCGTCGGGCTCGACATCGGCAAGGTGTGGGTCGCGGACGA

CGGCGCCGCGGTGGCGGTCTGGACCACGCCGGAGAGCGTCGAAGCGGGGG

CGGTGTTCGCCGAGATCGGCCCGCGCATGGCCGAGTTGAGCGGTTCCCGG

CTGGCCGCGCAGCAACAGATGGAAGGCCTCCTGGCGCCGCACCGGCCCAA

GGAGCCCGCGTGGTTCCTGGCCACCGTCGGCGTCTCGCCCGACCACCAGG

GCAAGGGTCTGGGCAGCGCCGTCGTGCTCCCCGGAGTGGAGGCGGCCGAG

CGCGCCGGGGTGCCCGCCTTCCTGGAGACCTCCGCGCCCCGCAACCTCCC

CTTCTACGAGCGGCTCGGCTTCACCGTCACCGCCGACGTCGAGGTGCCCG

AAGGACCGCGCACCTGGTGCATGACCCGCAAGCCCGGTGCCTGATAGAAC

TTGTTTATTGCAGCTTATAATGGTTACAAATAAAGCAATAGCATCACAAA

TTTCACAAATAAAGCATTTTTTTCACTGCATTCTAGTTGTGGTTTGTCCA

AACTCATCAATGTATCTTATCATGTCTGATAACTTCGTATAATGTATGCT

ATACGAAGTTATGCGGCCGCAATCGTCGACCTGCAGGCATGCAAGCTTAT

TGATTATTGACTAGTTATTAATAGTAATCAATTACGGGGTCATTAGTTCA

TAGCCCATATATGGAGTTCCGCGTTACATAACTTACGGTAAATGGCCCGC

CTGGCTGACCGCCCAACGACCCCCGCCCATTGACGTCAATAATGACGTAT

GTTCCCATAGTAACGCCAATAGGGACTTTCCATTGACGTCAATGGGTGGA

GTATTTACGGTAAACTGCCCACTTGGCAGTACATCAAGTGTATCATATGC

CAAGTACGCCCCCTATTGACGTCAATGACGGTAAATGGCCCGCCTGGCAT
```

-continued

TATGCCCAGTACATGACCTTATGGGACTTTCCTACTTGGCAGTACATCTA
CGTATTAGTCATCGCTATTACCATGGTCGAGGTGAGCCCCACGTTCTGCT
TCACTCTCCCCATCTCCCCCCCCTCCCCACCCCCAATTTTGTATTTATTT
ATTTTTTAATTATTTTGTGCAGCGATGGGGGCGGGGGGGGGGGGGGCGC
GCGCCAGGCGGGGCGGGGCGGGGCGAGGGGCGGGGCGGGGCGAGGCGGAG
AGGTGCGGCGGCAGCCAATCAGAGCGGCGCGCTCCGAAAGTTTCCTTTTA
TGGCGAGGCGGCGGCGGCGGCGCCCTATAAAAAGCGAAGCGCGCGGCGG
GCGGGAGTCGCTGCGCGCTGCCTTCGCCCCGTGCCCCGCTCCGCCGCCGC
CTCGCGCCGCCCGCCCCGGCTCTGACTGACCGCGTTACTCCCACAGGTGA
GCGGGCGGGACGGCCCTTCTCCTCCGGGCTGTAATTAGCGCTTGGTTTAA
TGACGGCTTGTTTCTTTTCTGTGGCTGCGTGAAAGCCTTGAGGGGCTCCG
GGAGGGCCCTTTGTGCGGGGGAGCGGCTCGGGGGGTGCGTGCGTGTGTG
TGTGCGTGGGGAGCGCCGCGTGCGGCTCCGCGCTGCCCGGCGGCTGTGAG
CGCTGCGGGCGCGGCGCGGGGCTTTGTGCGCTCCGCAGTGTGCGCGAGGG
GAGCGCGGCCGGGGCGGTGCCCCGCGGTGCGGGGGGCTGCGAGGGGAA
CAAAGGCTGCGTGCGGGGTGTGTGCGTGGGGGGGTGAGCAGGGGGTGTGG
GCGCGTCGGTCGGGCTGCAACCCCCCCTGCACCCCCCTCCCCGAGTTGCT
GAGCACGGCCCGGCTTCGGGTGCGGGCTCCGTACGGGGCGTGGCGCGGG
GCTCGCCGTGCCGGCGGGGGTGGCGGCAGGTGGGGGTGCCGGGCGGGG
CGGGGCCGCCTCGGGCCGGGAGGGCTCGGGGAGGGGCGCGGCGGCCCC
CGGAGCGCCGGCGGCTGTCGAGGCGCGGCGAGTCGCAGCCATTGCCTTTT
ATGGTAATCGTGCGAGAGGGCGCAGGGACTTCCTTTGTCCCAAATCTGTG
TGGAGCCGAAATCTGGGAGGCGCCGCCGCACCCCCTCTAGCGGGCGCGGG
GCGAAGCGGTGCGGCGCCGGCAGGAAGGAAATGGGCGGGAGGGCCTTCG
TGCGTCGCCGCGCCGCCGTCCCCTTCTCCCTCTCCAGCCTCGGGGCTGTC
CGCGGGGGGCGGCTGCCTTCGGGGGGACGGGGCAGGGCGGGGTTCGGC
TTCTGGCGTGTGACCGGCGGCTCTAGAGCCTCTGCTAACCATGTTCATGC
CTTCTTCTTTTTCCTACAGCTCCTGGGCAACGTGCTGGTTATTGTGCTGT
CTCATCATTTTGGCAAAGAATTCCTCGACCTCGAGATGCCCAAGCCCTG
CCCTGGCTCCTGCTGTGGATGGGCGCGGGAGTGCTGCCTGCCCACGGCAC
CCAGCACGGCATCCGGCTGCCCCTGCGCAGCGGCCTGGGGGGCGCCCCCC
TGGGGCTGCGGCTGCCCCGGGAGACCGACGAAGAGCCCGAGGAGCCCGGC
CGGAGGGGCAGCTTTGTGGAGATGGTGGACAACCTGAGGGGCAAGTCGGG
GCAGGGCTACTACGTGGAGATGACCGTGGGCAGCCCCCGCAGACGCTCA
ACATCCTGGTGGATACAGGCAGCAGTAACTTTGCAGTGGGTGCTGCCCCC
CACCCCTTCCTGCATCGCTACTACCAGAGGCAGCTGTCCAGCACATACCG
GGACCTCCGGAAGGGTGTGTATGTGCCCTACACCCAGGGCAAGTGGGAAG
GGGAGCTGGGCACCGACCTGCTTTGTGGTGCTGGCTTCCCCCTCAACCAG
TCTGAAGTGCTGGCCTCTGTCGGAGGGAGCATGATCATTGGAGGTATCGA
CCACTCGCTGTACACAGGCAGTCTCTGGTATACACCCATCCGGCGGGAGT
GGTATTATGAGGTGATCATTGTGCGGGTGGAGATCAATGGACAGGATCTG

-continued

AAAATGGACTGCAAGGAGTACAACTATGACAAGAGCATTGTGGACAGTGG
CACCACCAACCTTCGTTTGCCCAAGAAAGTGTTTGAAGCTGCAGTCAAAT
CCATCAAGGCAGCCTCCTCCACGGAGAAGTTCCCTGATGGTTTCTGGCTA
GGAGAGCAGCTGGTGTGCTGGCAAGCAGGCACCACCCCTTGGAACATTTT
CCCAGTCATCTCACTCTACCTAATGGGTGAGGTTACCAACCAGTCCTTCC
GCATCACCATCCTTCCGCAGCAATACCTGCGGCCAGTGGAAGATGTGGCC
ACGTCCCAAGACGACTGTTACAAGTTTGCCATCTCACAGTCATCCACGGG
CACTGTTATGGGAGCTGTTATCATGGAGGGCTTCTACGTTGTCTTTGATC
GGGCCCGAAAACGAATTGGCTTTGCTGTCAGCGCTTGCCATGTGCACGAT
GAGTTCAGGACGGCAGCGGTGGAAGGCCCTTTTGTCACCTTGGACATGGA
AGACTGTGGCTACAACATTCCACAGACAGATGAGTCAACCCTCATGACCA
TAGCCTATGTCATGGCTGCCATCTGCGCCCTCTTCATGCTGCCACTCTGC
CTCATGGTGTGTCAGTGGCGCTGCCTCCGCTGCCTGCGCCAGCAGCATGA
TGACTTTGCTGATGACATCTCCCTGCTGAAGGTCGACAGATCTGGCAGCG
GAGAGGGCAGAGGAAGTCTTCTAACATGCGGTGACGTGGAGGAGAATCCC
GGCCCTAGGTTCGAAATGGTGAGCAAGGGCGAGGAGCTGTTCACCGGGGT
GGTGCCCATCCTGGTCGAGCTGGACGGCGACGTAAACGGCCACAAGTTCA
GCGTGTCCGGCGAGGGCGAGGGCGATGCCACCTACGGCAAGCTGACCCTG
AAGTTCATCTGCACCACCGGCAAGCTGCCCGTGCCCTGGCCCACCCTCGT
GACCACCTTGACCTACGGCGTGCAGTGCTTCGCCCGCTACCCCGACCACA
TGAAGCAGCACGACTTCTTCAAGTCCGCCATGCCCGAAGGCTACGTCCAG
GAGCGCACCATCTTCTTCAAGGACGACGGCAACTACAAGACCCGCGCCGA
GGTGAAGTTCGAGGGCGACACCCTGGTGAACCGCATCGAGCTGAAGGGCA
TCGACTTCAAGGAGGACGGCAACATCCTGGGGCACAAGCTGGAGTACAAC
TACAACAGCCACAAGGTCTATATCACCGCCGACAAGCAGAAGAACGGCAT
CAAGGTGAACTTCAAGACCCGCCACAACATCGAGGACGGCAGCGTGCAGC
TCGCCGACCACTACCAGCAGAACACCCCCATCGGCGACGGCCCCGTGCTG
CTGCCCGACAACCACTACCTGAGCACCCAGTCCGCCCTGAGCAAAGACCC
CAACGAGAAGCGCGATCACATGGTCCTGCTGGAGTTCGTGACCGCCGCCG
GGATCACTCTCGGCATGGACGAGCTGTACAAGTGAGAGCTCCTCGACTGT
GCCTTCTAGTTGCCAGCCATCTGTTGTTTGCCCCTCCCCCGTGCCTTCCT
TGACCCTGGAAGGTGCCACTCCCACTGTCCTTTCCTAATAAAATGAGGAA
ATTGCATCGCATTGTCTGAGTAGGTGTCATTCTATTCTGGGGGGTGGGGT
GGGGCAGGACAGCAAGGGGGAGGATTGGGAAGACAATAGCAGGCATGCGA
TCG.

Sequence at the 5'end junction between the insert and host genome is denoted as:

(SEQ ID NO. 11)
ACCCCACAGTGGGGCAAGCTTGGATCCTC
and its complementary sequence.

Sequence at the 3'end junction between the insert and host genome is denoted as:

(SEQ ID NO. 12)
CGATCGGCGGCCGCTACTAGGGACAGGATT
and its complementary sequence.

In one specific embodiment, an hiPSC line made by the method of the present invention has an exogenous nucleic acid sequence integrated at AAVS1 site. The nucleic acid sequence comprises a PGK-1 promoter, a puromycin gene, a CAG promoter, a mutant PS1 gene (PS1dE9), and a GFP gene and sequences that link different segments. The inserted nucleic acid sequence is described below (the underlined part is PS1dE9 gene):

(SEQ ID NO. 13)
ATAACTTCGTATAATGTATGCTATACGAAGTTATTACCGGGTAGGGGAGG
CGCTTTTCCCAAGGCAGTCTGGAGCATGCGCTTTAGCAGCCCCGCTGGGC
ACTTGGCGCTACACAAGTGGCCTCTGGCCTCGCACACATTCCACATCCCC
CGGTAGGCGCCAACCGGCTCCGTTCTTTGGTGGCCCCTTCGCGCCACCTT
CTACTCCTCCCCTAGTCAGGAAGTTCCCCCCCGCCCCGCAGCTCGCGTCG
TGCAGGACGTGACAAATGGAAGTAGCACGTCTCACTAGTCTCGTGCAGAT
GGACAGCACCGCTGAGCAATGGAAGCGGGTAGGCCTTTGGGGCAGCGGCC
AATAGCAGCTTTGCTCCTTCGCTTTCTGGGCTCAGAGGCTGGGAAGGGGT
GGGTCCGGGGGCGGGCTCAGGGGCGGGCTCAGGGGCGGGGCGGGCGCCCG
AAGGTCCTCCGGAGGCCCGGCATTCTGCACGCTTCAAAAGCGCACGTCTG
CCGCGCTGTTCTCCTCTTCCTCATCTCCGGGCCTTTCGGAATTCATGACC
GAGTACAAGCCCACGGTGCGCCTCGCCACCCGCGACGACGTCCCCCGGGC
CGTACGCACCCTCGCCGCCGCGTTCGCCGACTACCCCGCCACGCGCCACA
CCGTCGACCCGGACCGCCACATCGAGCGGGTCACCGAGCTGCAAGAACTC
TTCCTCACGCGCGTCGGGCTCGACATCGGCAAGGTGTGGGTCGCGGACGA
CGGCGCCGCGGTGGCGGTCTGGACCACGCCGGAGAGCGTCGAAGCGGGGG
CGGTGTTCGCCGAGATCGGCCCGCGCATGGCCGAGTTGAGCGGTTCCCGG
CTGGCCGCGCAGCAACAGATGGAAGGCCTCCTGGCGCCGCACCGGCCCAA
GGAGCCCGCGTGGTTCCTGGCCACCGTCGGCGTCTCGCCCGACCACCAGG
GCAAGGGTCTGGGCAGCGCCGTCGTGCTCCCCGGAGTGGAGGCGGCCGAG
CGCGCCGGGGTGCCCGCCTTCCTGGAGACCTCCGCGCCCCGCAACCTCCC
CTTCTACGAGCGGCTCGGCTTCACCGTCACCGCCGACGTCGAGGTGCCCG
AAGGACCGCGCACCTGGTGCATGACCCGCAAGCCCGGTGCCTGATAGAAC
TTGTTTATTGCAGCTTATAATGGTTACAAATAAAGCAATAGCATCACAAA
TTTCACAAATAAAGCATTTTTTCACTGCATTCTAGTTGTGGTTTGTCCA
AACTCATCAATGTATCTTATCATGTCTGATAACTTCGTATAATGTATGCT
ATACGAAGTTATGCGGCCGCAATCGTCGACCTGCAGGCATGCAAGCTTAT
TGATTATTGACTAGTTATTAATAGTAATCAATTACGGGGTCATTAGTTCA
TAGCCCATATATGGAGTTCCGCGTTACATAACTTACGGTAAATGGCCCGC
CTGGCTGACCGCCCAACGACCCCCGCCCATTGACGTCAATAATGACGTAT

GTTCCCATAGTAACGCCAATAGGGACTTTCCATTGACGTCAATGGGTGGA
GTATTTACGGTAAACTGCCCACTTGGCAGTACATCAAGTGTATCATATGC
CAAGTACGCCCCCTATTGACGTCAATGACGGTAAATGGCCCGCCTGGCAT
TATGCCCAGTACATGACCTTATGGGACTTTCCTACTTGGCAGTACATCTA
CGTATTAGTCATCGCTATTACCATGGTCGAGGTGAGCCCCACGTTCTGCT
TCACTCTCCCCATCTCCCCCCCCTCCCCACCCCCAATTTTGTATTTATTT
ATTTTTTAATTATTTTGTGCAGCGATGGGGGCGGGGGGGGGGGGGGCGC
GCGCCAGGCGGGGCGGGGCGGGGCGAGGGGCGGGGCGGGGCGAGGCGGAG
AGGTGCGGCGGCAGCCAATCAGAGCGGCGCGCTCCGAAAGTTTCCTTTTA
TGGCGAGGCGGCGGCGGCGGCGGCCCTATAAAAAGCGAAGCGCGCGGCGG
GCGGGAGTCGCTGCGCGCTGCCTTCGCCCCGTGCCCCGCTCCGCCGCCGC
CTCGCGCCGCCCGCCCCGGCTCTGACTGACCGCGTTACTCCCACAGGTGA
GCGGGCGGGACGGCCCTTCTCCTCCGGGCTGTAATTAGCGCTTGGTTTAA
TGACGGCTTGTTTCTTTTCTGTGGCTGCGTGAAAGCCTTGAGGGGCTCCG
GGAGGGCCCTTTGTGCGGGGGGAGCGGCTCGGGGGGTGCGTGCGTGTGTG
TGTGCGTGGGGAGCGCCGCGTGCGGCTCCGCGCTGCCCGGCGGCTGTGAG
CGCTGCGGGCGCGGCGCGGGGCTTTGTGCGCTCCGCAGTGTGCGCGAGGG
GAGCGCGGCCGGGGCGGTGCCCCGCGGTGCGGGGGGGCTGCGAGGGGAA
CAAAGGCTGCGTGCGGGGTGTGTGCGTGGGGGGGTGAGCAGGGGGTGTGG
GCGCGTCGGTCGGGCTGCAACCCCCCCTGCACCCCCCTCCCCGAGTTGCT
GAGCACGGCCCGGCTTCGGGTGCGGGGCTCCGTACGGGGCGTGGCGCGGG
GCTCGCCGTGCCGGCGGGGGTGGCGGCAGGTGGGGGTGCCGGGCGGGG
CGGGGCCGCCTCGGGCCGGGAGGGCTCGGGGGAGGGGCGCGGCGGCCCC
CGGAGCGCCGGCGGCTGTCGAGGCGCGGCGAGTCGCAGCCATTGCCTTTT
ATGGTAATCGTGCGAGAGGGCGCAGGGACTTCCTTTGTCCCAAATCTGTG
TGGAGCCGAAATCTGGGAGGCGCCGCCGCACCCCCTCTAGCGGGCGCGGG
GCGAAGCGGTGCGGCGCCGGCAGGAAGGAAATGGGCGGGAGGGCCTTCG
TGCGTCGCCGCGCCGCCGTCCCCTTCTCCCTCTCCAGCCTCGGGGCTGTC
CGCGGGGGGCGGCTGCCTTCGGGGGGGACGGGGCAGGGCGGGGTTCGGC
TTCTGGCGTGTGACCGGCGGCTCTAGAGCCTCTGCTAACCATGTTCATGC
CTTCTTCTTTTTCCTACAGCTCCTGGGCAACGTGCTGGTTATTGTGCTGT
CTCATCATTTTGGCAAAGAATTCCTCGACCTCGAG<u>ATGACAGAGTTACCT</u>
<u>GCACCGTTGTCCTACTTCCAGAATGCACAGATGTCTGAGGACAACCACCT</u>
<u>GAGCAATACTGTACGTAGCCAGAATGACAATAGAGAACGGCAGGAGCACA</u>
<u>ACGACAGACGGAGCCTTGGCCACCCTGAGCCATTATCTAATGGACGACCC</u>
<u>CAGGGTAACTCCCGGCAGGTGGTGGAGCAAGATGAGGAAGAAGATGAGGA</u>
<u>GCTGACATTGAAATATGGCGCCAAGCATGTGATCATGCTCTTTGTCCCTG</u>
<u>TGACTCTCTGCATGGTGGTGGTCGTGGCTACCATTAAGTCAGTCAGCTTT</u>
<u>TATACCCGGAAGGATGGGCAGCTAATCTATACCCCATTCACAGAAGATAC</u>
<u>CGAGACTGTGGGCCAGAGAGCCCTGCACTCAATTCTGAATGCTGCCATCA</u>
<u>TGATCAGTGTCATTGTTGTCATGACTATCCTCCTGGTGGTTCTGTATAAA</u>

-continued

TACAGGTGCTATAAGGTCATCCATGCCTGGCTTATTATATCATCTCTATT

GTTGCTGTTCTTTTTTTCATTCATTTACTTGGGGGAAGTGTTTAAAACCT

ATAACGTTGCTGTGGACTACATTACTGTTGCACTCCTGATCTGGAATTTT

GGTGTGGTGGGAATGATTTCCATTCACTGGAAAGGTCCACTTCGACTCCA

GCAGGCATATCTCATTATGATTAGTGCCCTCATGGCCCTGGTGTTTATCA

AGTACCTCCCTGAATGGACTGCGTGGCTCATCTTGGCTGTGATTTCAGTA

TATGATTTAGTGGCTGTTTTGTGTCCGAAAGGTCCACTTCGTATGCTGGT

TGAAACAGCTCAGGAGAGAAATGAAACGCTTTTTCCAGCTCTCATTTACT

CCTGCACAGAAAGGGAGTCACAAGACACTGTTGCAGAGAATGATGATGGC

GGGTTCAGTGAGGAATGGGAAGCCCAGAGGGACAGTCATCTAGGGCCTCA

TCGCTCTACACCTGAGTCACGAGCTGCTGTCCAGGAACTTTCCAGCAGTA

TCCTCGCTGGTGAAGACCCAGAGGAAAGGGGAGTAAAACTTGGATTGGGA

GATTTCATTTTCTACAGTGTTCTGGTTGGTAAAGCCTCAGCAACAGCCAG

TGGAGACTGGAACACAACCATAGCCTGTTTCGTAGCCATATTAATTGGTT

TGTGCCTTACATTATTACTCCTTGCCATTTTCAAGAAAGCATTGCCAGCT

CTTCCAATCTCCATCACCTTTGGGCTTGTTTTCTACTTTGCCACAGATTA

TCTTGTACAGCCTTTTATGGACCAATTAGCATTCCATCAATTTTATATCT

AGAGATCTGGCAGCGGAGAGGGCAGAGGAAGTCTTCTAACATGCGGTGAC

GTGGAGGAGAATCCCGGCCCTAGGTTCGAAATGGTGAGCAAGGGCGAGGA

GCTGTTCACCGGGGTGGTGCCCATCCTGGTCGAGCTGGACGGCGACGTAA

ACGGCCACAAGTTCAGCGTGTCCGGCGAGGGCGAGGGCGATGCCACCTAC

GGCAAGCTGACCCTGAAGTTCATCTGCACCACCGGCAAGCTGCCCGTGCC

CTGGCCCACCCTCGTGACCACCTTGACCTACGGCGTGCAGTGCTTCGCCC

GCTACCCCGACCACATGAAGCAGCACGACTTCTTCAAGTCCGCCATGCCC

GAAGGCTACGTCCAGGAGCGCACCATCTTCTTCAAGGACGACGGCAACTA

CAAGACCCGCGCCGAGGTGAAGTTCGAGGGCGACACCCTGGTGAACCGCA

TCGAGCTGAAGGGCATCGACTTCAAGGAGGACGGCAACATCCTGGGGCAC

AAGCTGGAGTACAACTACAACAGCCACAAGGTCTATATCACCGCCGACAA

GCAGAAGAACGGCATCAAGGTGAACTTCAAGACCCGCCACAACATCGAGG

ACGGCAGCGTGCAGCTCGCCGACCACTACCAGCAGAACACCCCCATCGGC

GACGGCCCCGTGCTGCTGCCCGACAACCACTACCTGAGCACCCAGTCCGC

CCTGAGCAAAGACCCCAACGAGAAGCGCGATCACATGGTCCTGCTGGAGT

TCGTGACCGCCGCCGGGATCACTCTCGGCATGGACGAGCTGTACAAGTGA

GAGCTCCTCGACTGTGCCTTCTAGTTGCCAGCCATCTGTTGTTTGCCCCT

CCCCCGTGCCTTCCTTGACCCTGGAAGGTGCCACTCCCACTGTCCTTTCC

TAATAAAATGAGGAAATTGCATCGCATTGTCTGAGTAGGTGTCATTCTAT

TCTGGGGGGTGGGGTGGGGCAGGACAGCAAGGGGGAGGATTGGGAAGACA

ATAGCAGGCATGCGATCG.

Sequence at the 5'end junction between the insert and host genome is denoted as:

(SEQ ID NO. 11)
ACCCCACAGTGGGGCAAGCTTGGATCCTC
and its complementary sequence

Sequence at the 3'end junction between the insert and host genome is denoted as:

(SEQ ID NO. 12)
CGATCGGCGGCCGCTACTAGGGACAGGATT
and its complementary sequence.

In another embodiment, the inserted nucleic acid sequence may contain sequence that encodes any variant of BACE1 and/or any variant of PS1. The variants include, for instance, naturally-occurring variants due to allelic variations between individuals (e.g., polymorphisms), alternative splicing forms, etc. Variants are preferably substantially homologous to sequences according to the present invention, i.e., exhibit a nucleotide sequence identity of typically at least about 80%, preferably at least about 90%, more preferably at least about 95% with sequences of the present invention. Variants of the genes of the present invention also include nucleic acid sequences, which hybridize to a sequence as defined above (or a complementary strand thereof) under stringent hybridization conditions. Typical stringent hybridization conditions include temperatures above 42° C. and salinity of equal or less than 200 mM.

Drug Screening Method

In one embodiment the present disclosure relates to a process of using hiPSC lines created by the method of the present invention to screen therapeutic agents for treatment of AD. The process may include multiple steps of re-differentiating hiPSC line into functional neurons, administrating drug compounds into the neuron culture media, culturing neurons in presence of drug compounds for a period of time, and measuring beta-secretase level, Abeta-40 concentration, Abeta-42 concentration, and Abeta-42/Abeta-40 ratio, etc.

The measurement of beta-secretase can be conducted by testing the expression of BACE1 gene at RNA and protein levels by conventional methods in the art.

In one specific embodiment, a hiPSC line that over-expresses BACE1 gene will be used to produce large quantities of functional neurons. Neuronal cells derived from the hiPSC line will be cultured in a 96-well plate. Compounds to be screened will be added to the neurons culture for 2 days to 2 weeks. The effect of a compound on reduction of beta-secretase and/or Abeta-42 peptides will be measured in parallel.

In another specific embodiment, an hiPSC line that over-expresses PS1dE9 gene will be used to produce large quantities of functional neurons. Neuronal cells derived from the hiPSC line will be cultured in a 96-well plate. Compounds to be screened will be added to the neurons culture for 2 days to 2 weeks. The effect of a compound on reduction of Abeta-42 peptides will be measured.

In another embodiment, a hiPSC line that over-expresses any variant of BACE1 gene and/or any variant of PS1 gene at AAVS1 site will be used to produce large quantities of functional neurons. The variants include, for instance, naturally-occurring variants due to allelic variations between individuals (e.g., polymorphisms), alternative splicing forms, etc. Variants are preferably substantially homologous to sequences according to the present invention, i.e., exhibit a nucleotide sequence identity of typically at least about 80%, preferably at least about 90%, more preferably at least about 95% with sequences of the present invention. Variants of the genes of the present invention also include nucleic acid sequences, which hybridize to a sequence as defined above (or a complementary strand thereof) under stringent hybridization conditions. Typical stringent hybridization conditions include temperatures above 42° C. and salinity of equal or less than 200 mM.

Reference will be made in detail to embodiments of the present disclosure. The embodiments described herein with reference to drawings are explanatory, illustrative, and used to generally understand the present disclosure. The embodiments shall not be construed to limit the present disclosure. The same or similar elements and the elements having same or similar functions are denoted by like reference numerals throughout the descriptions. It is also to be understood that the terminology used herein is for the purpose of describing particular embodiments only, and is not intended to be limiting, since the scope of the present invention will be limited only by the appended claims.

EXAMPLES

The examples are provided only with a purpose of illustration.

Example 1: Generation of Parental hiPSC Lines for Genome Editing

Two hiPSC lines, UCIS3007 and iPSN0041, were generated and used as parental hiPSC lines for making isogenic diseased hiPSC lines. UCIS3007 was derived from urine cells of a non-diseased female donor by a retrovirus vector-mediated reprogramming method that uses four transcription factors (Oct4, Sox1, Klf4, and cMyc). The donor urine epithelial cells were cultured with urine epithelial cell proliferation medium (CIB, cat #UC-0302). About 20,000 urine epithelial cells were inoculated into 12-well plates one day before the virus infection. The cells transfected with retroviral vectors were cultured with the hiPSC re-programming serum medium (CIB, Cat #. RE-0201). On day 6, the cells were plated onto a T25 flask containing feeder cells and treated with mitomycin C. About 10,000 cells were seeded in each T25 flask and cultured with reprogramming medium for about 20 days until hiPSC clones appears. Then, the clones were picked up onto Matrigel (Corning Cat #352477) coated plates for further purification and expansion.

iPSN0041 was derived from umbilical cord matrix cells of a non-diseased donor by a footprint-free method using episomal vector with six transcription factors. About one million umbilical cord matrix cells were electrotransfered with episome plasmids (3 µg pCEP4-EO2S-EN2K, 2.4 µg pCEP4-M2L, 3.2 µg pCEP4-EO2S-1) mixed with a nuclear transfer reagent (Lonza, Cat. No. VPI-1005) using Amaxa Nucleofector kit II. The transfected cells were immediately inoculated into two T25 flasks coated with Matrigel (Corning Cat #352477), cultured with hiPSC reprogramming medium (CIB, Cat. No. RE-0202). The medium was changed to mTeSR1 on the 15th day after transfection and cultured for additional 7 days until hiPSC colonies appear. Clones with typical hiPSC morphology were selected for further purification and expansion.

Figure 1:
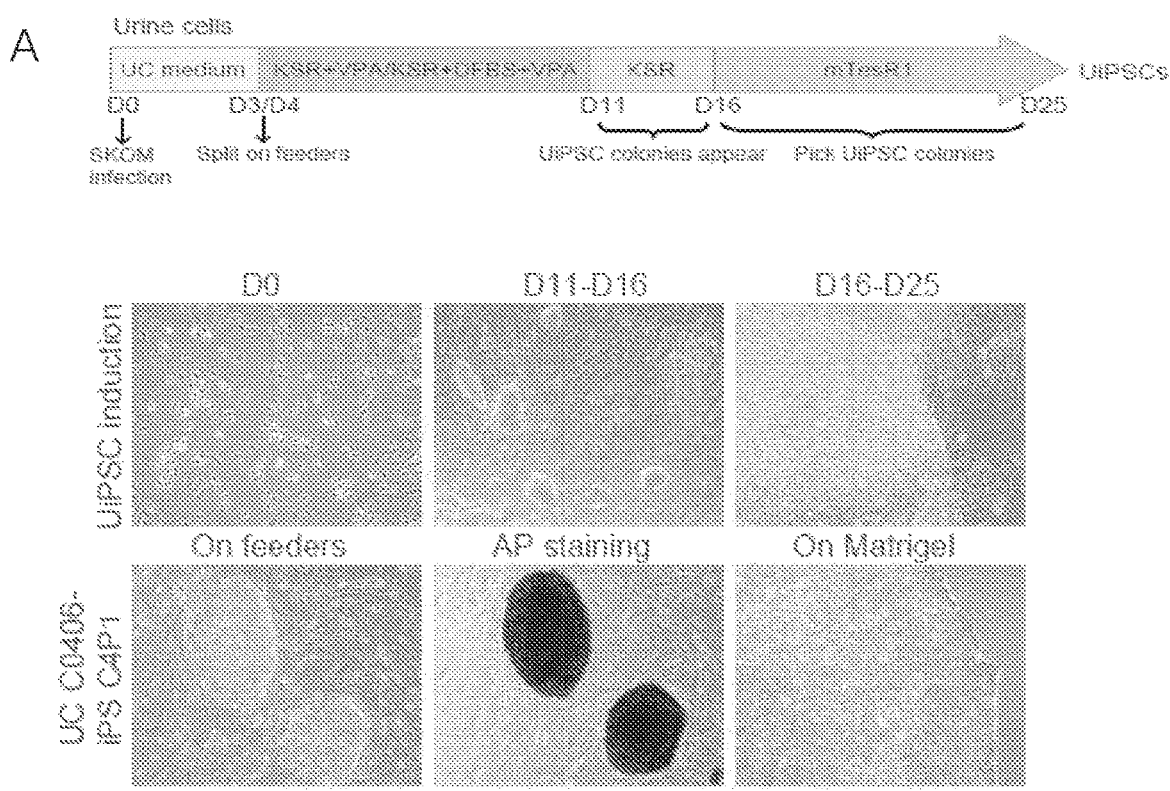
FIGS. 1A-1F Example for generation and characterization of the parental hiPSC lines (UCIS3007): Urine cells from a healthy non-diseased donor are isolated and converted into hiPSC cell by the standard reprogramming method using 4 transcription factors (Oct4, Sox2, Klf4, and cMyc).
Figure 1:
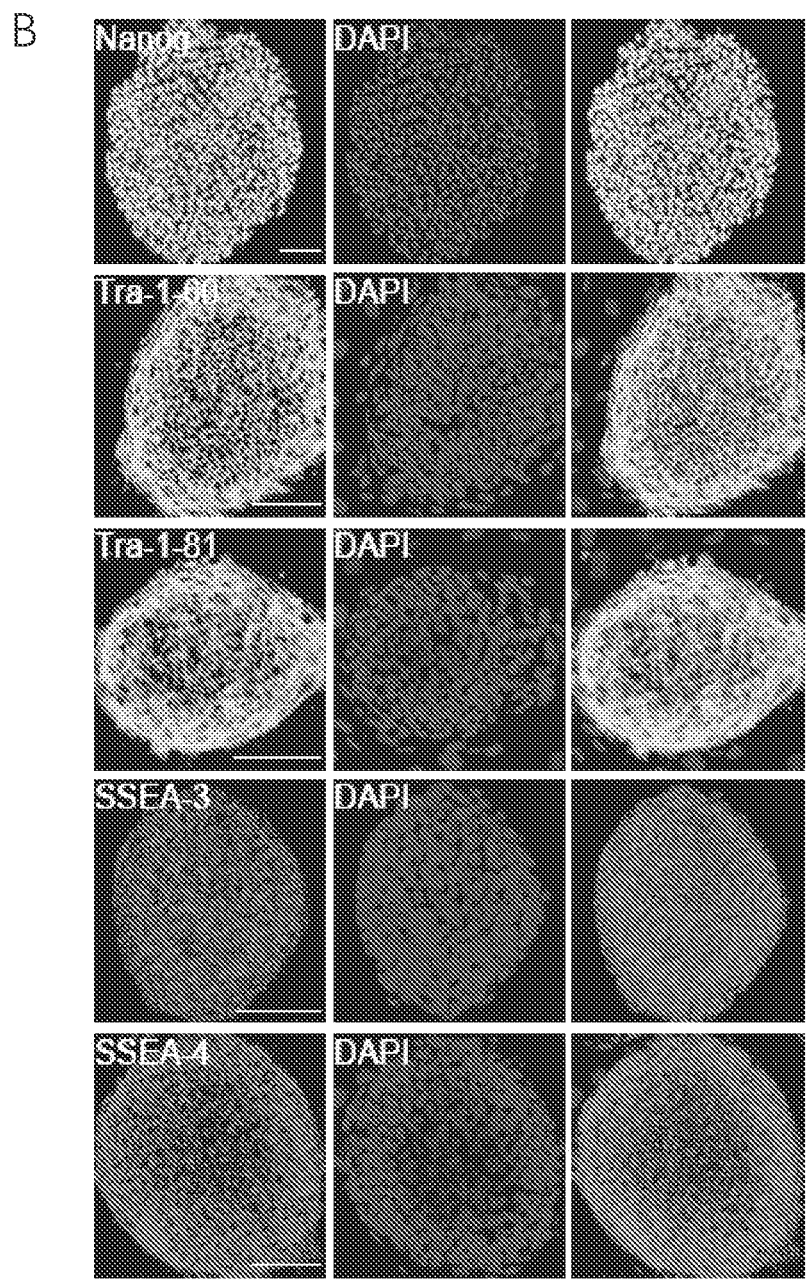
Figure 1:
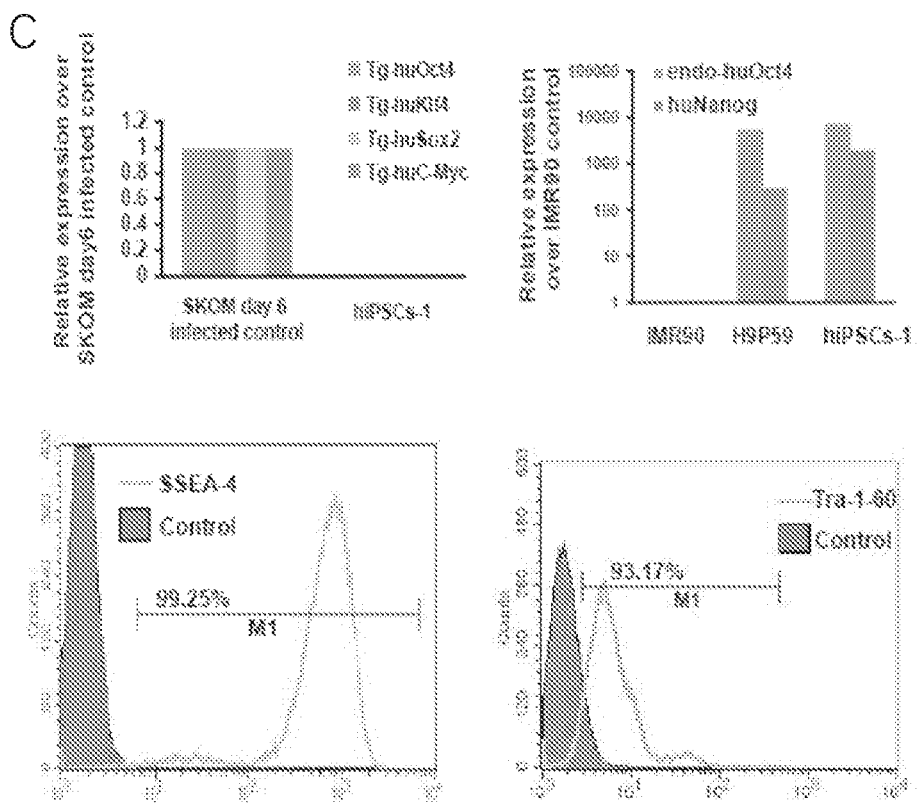
Figure 1:
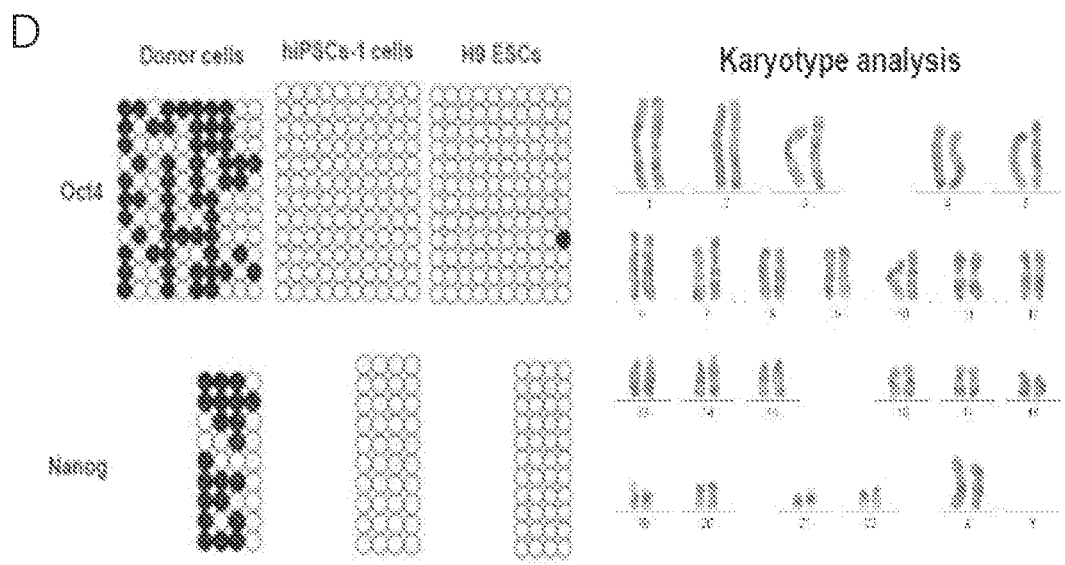
Figure 1:
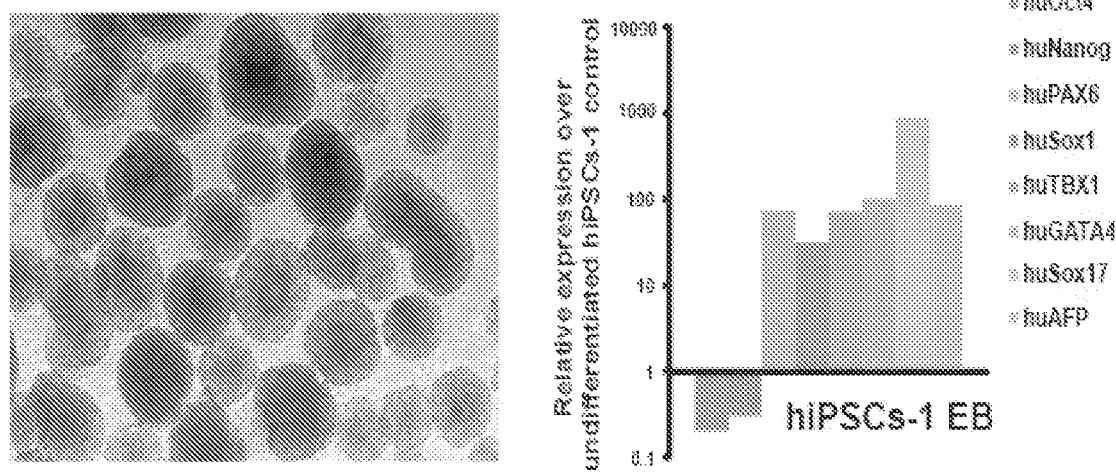
Figure 1:
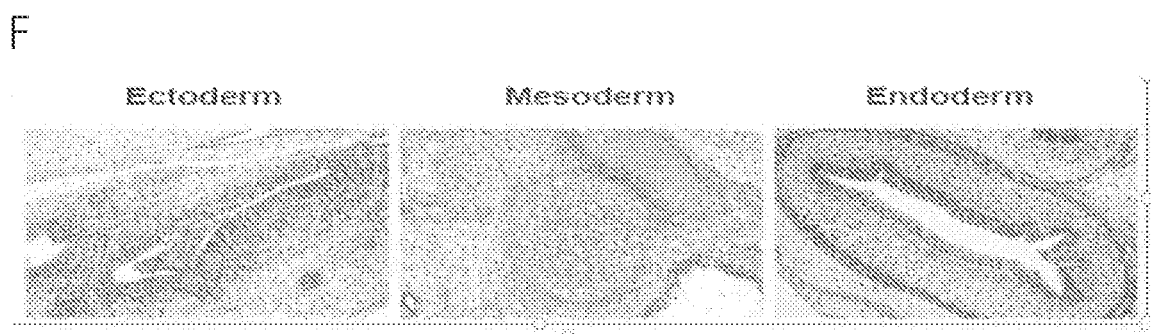
Figure 2:
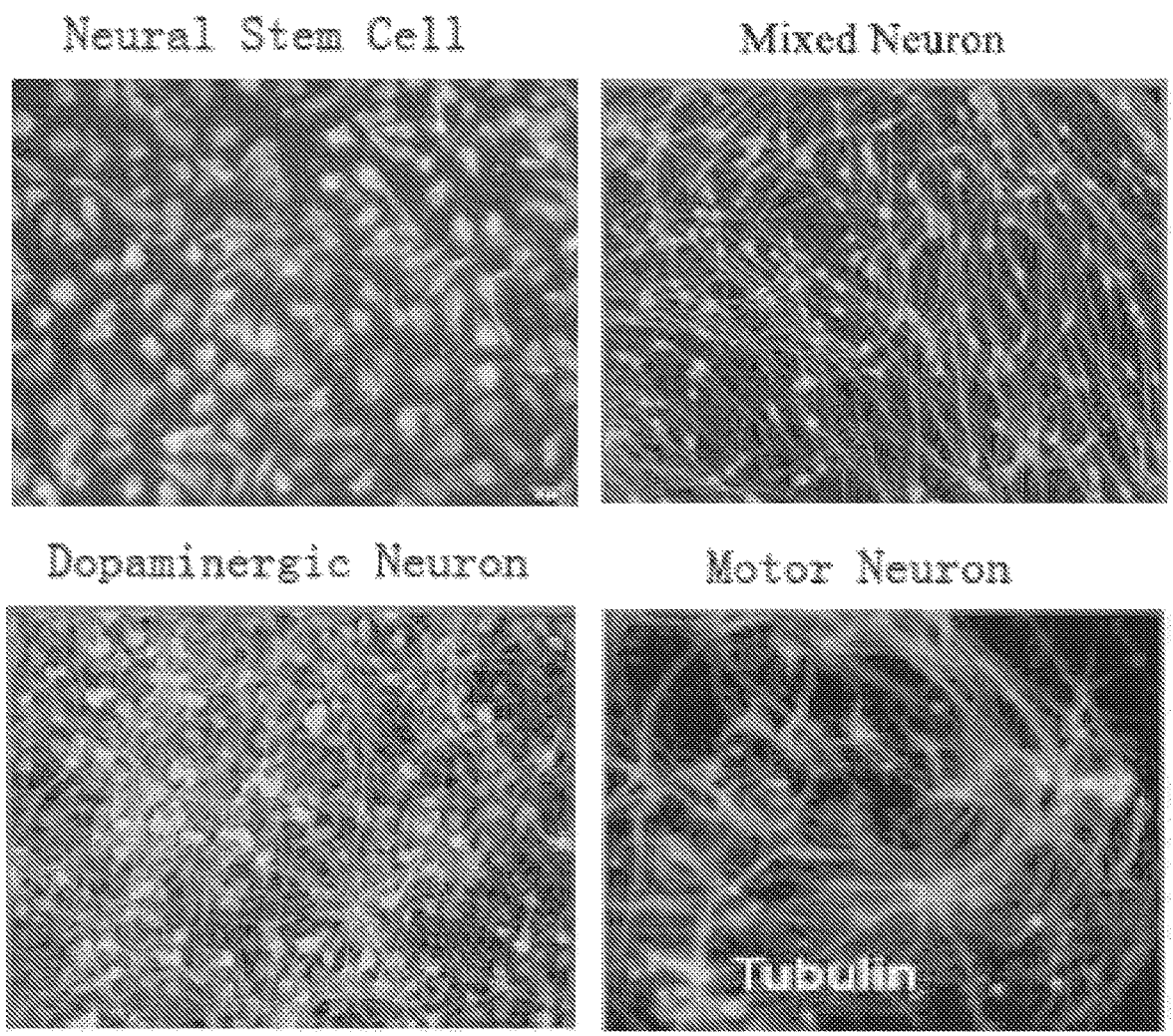
FIG. 2 Neural stem cells and neuronal cells (NSC, mixed neuron, dopaminergic neuron and motor neuron) derived from the parental hiPSC lines.

Characterization of hiPSC clones were followed the international standard (ref 43-44), including exogenous gene silencing and pluripotency marker expression detection, exogenous gene integration assays, promoter demethylation analysis, karyotyping test, differentiation potential test (embryoid body formation), teratoma test, and cell ID (STR) test (ref 43-44), etc. (FIGS. 1A-1F). In addition, the neural lineage differentiation potential for these two parental hiPSC lines was also validated before conducting genome editing work (FIG. 2).

Example 2: Construction of Donor Vector and Targeting Vectors hiPSC genetic engineering was conducted using the most commonly used genome editing technology, CRISPR/Cas9 system. For targeted integration of AD-related genes into a safe harbor site (AAVS1 site), a specific CRISPR sgRNA vector targeted the AAVS1 site was constructed. sgRNA design and construction followed the method described in literature (ref 29). The target site of the BpiI enzyme is located on the vector and the recognition site is at the cleavage moiety. Therefore, the target site spacer sequence can be cloned into the vector by one step digestion. The vector contains 5'GTGG3' and 5'GTTT3' cohesive ends after digestion. By synthesizing the cohesive end of the CACC+ target spacer sequence and the cohesive terminal AAAC+ reverse complement sequence, sgRNA becomes a double stranded oligo sequence with additional cohesive ends, which can be connected to the cas9 vector. CRISPR-cas9 plasmid is generally constructed by a two-step method. The first step is to treat the synthesis of the cleavage site of oligo sequence. The second step is to ligate the treated oligo sequence with the CRISPR-Cas9 vector treated by restriction enzyme digestion.

Figure 3:
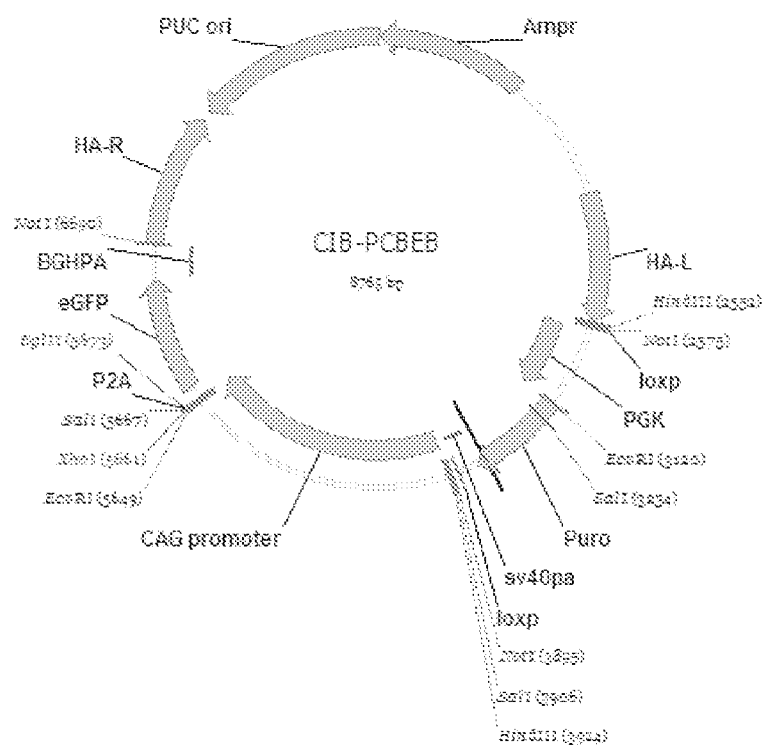
FIGS. 3A-3C Map of donor vector used for generating hiPSC lines with ectopic expression of AD-related gene at AAVS1 site. The nucleic acid sequence involved in targeted integration comprises a homologous sequence to human AAVS1 site (HA-L and HA-R), a human PGK-1 promoter, a drug selection marker gene, a CAG promoter, an AD-related gene and a reporter gene, all in a cis fashion. Different AD-related genes can be easily replaced by restriction enzyme digestion using Xho-I and BglII.
Figure 3:
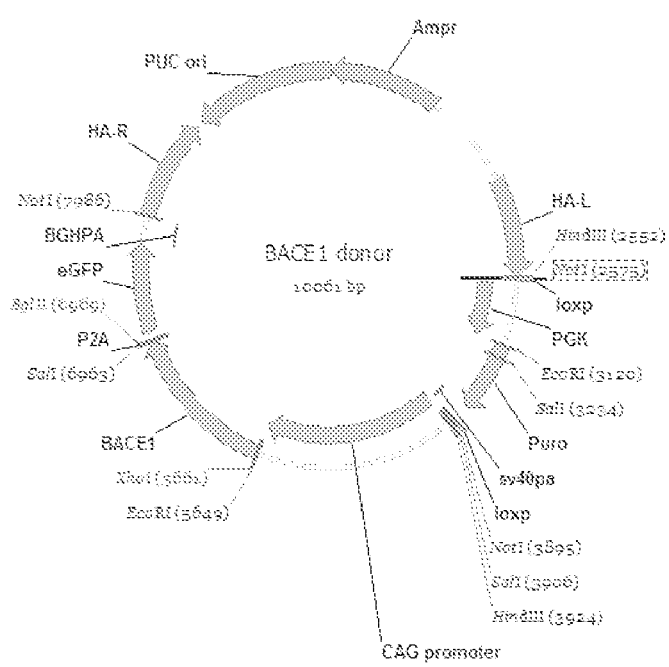
Figure 3:
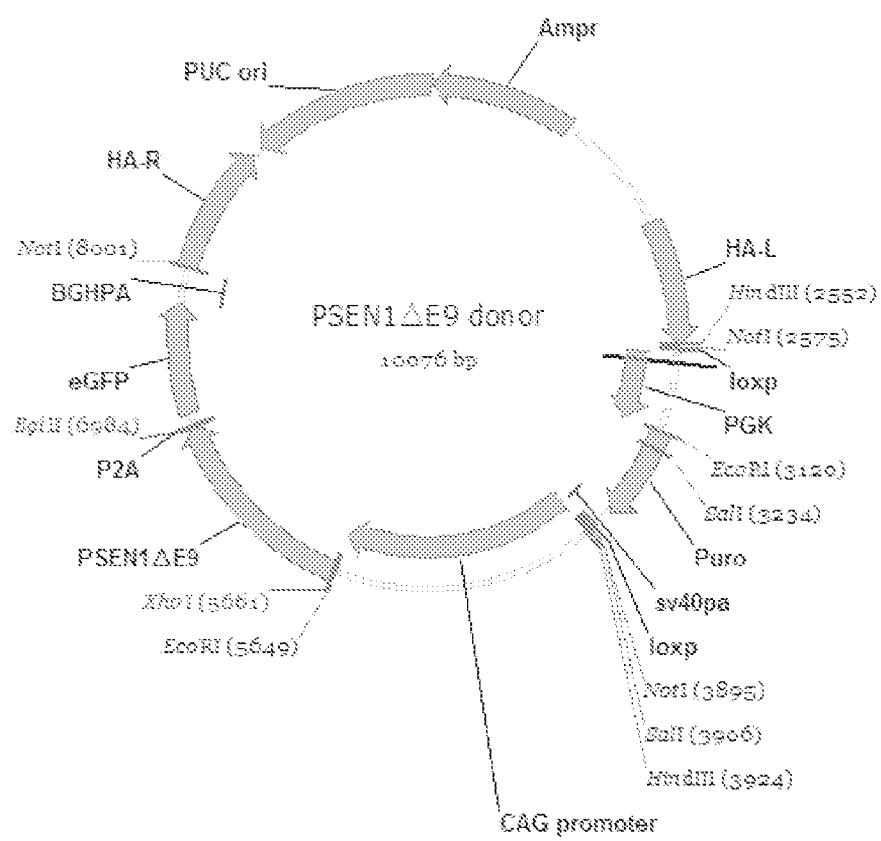

For donor construction, a backbone vector that comprises PGK-PURO-SV40PA, P2A-EGFP-BGHPA and CAG promoters, and a multiple cloning site (MSC) was generated first. To construct the final donor, five plasmids were generated: 1) T-HindIII-CAG-EcoRI; 2) T-SalI-P2A-EGFP-BGHPA-NotI; 3) T-HindIII-PGK-PURO-SV40PA-HindIII; 4) Synthetic PUC19-EcoRI-BACE1cds-SalI; and 5) PZD vector (Sigma-Aldrich). The first step is to digest plasmid 1, 2, 4, and 5, recover four fragments, HindIII-CAG-EcoRI-, -LALI-EGA-EGFP-BGHPA-NotI-, EcoRI-BACE1cds-SalI-, and HindIII-PZDonor-HindIII-, and then ligate all fragments together. After transformation into DH5α cell the positive clones were identified as the intermediate vector of PCBEB6. The final donor vector was generated by HindIII digestion and then ligation of PCBEB6 and T-HindIII-PGK-PURO-SV40PA-HindIII. This donor vector is named as CIB-PCBEB (FIG. 3A). All exogenous genes for over-expression at AAVS1 site was done by synthesizing the gene sequence with BglII and XhoI cleavage sites at both ends. The gene of interest is inserted into the vector by digestion of the vector with BglII and XhoI, and then ligation of the insert with the vector. The final donor plasmid was used to transform DH5α cell and then verified by sequencing. Donor constructs for over-expression of BACE1 gene and PS1dE9 gene were shown in FIGS. 3B and 3C.

Example 3: Targeted Integration of AD-Related Genes at AAVS1 Site

Figure 5:
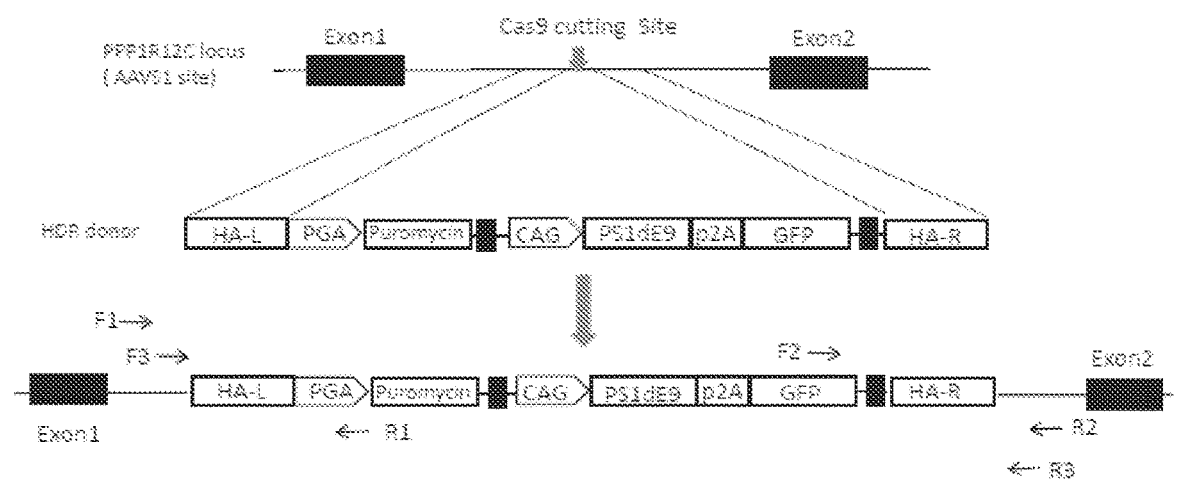
FIGS. 5A-5C. Targeted integration of PS1dE9 gene into AAVS1 site. AAVS1 site is located in the intron region of Exon 1 and Exon 2 of PPP1R12C locus. F1, F2, F3, R1, R2, and R3 are primers used for verification of insertion by junction PCR.
FIG. 5D. Over-expression of PS1dE9 gene in iPSC (UCIS3007-74).
Figure 5:
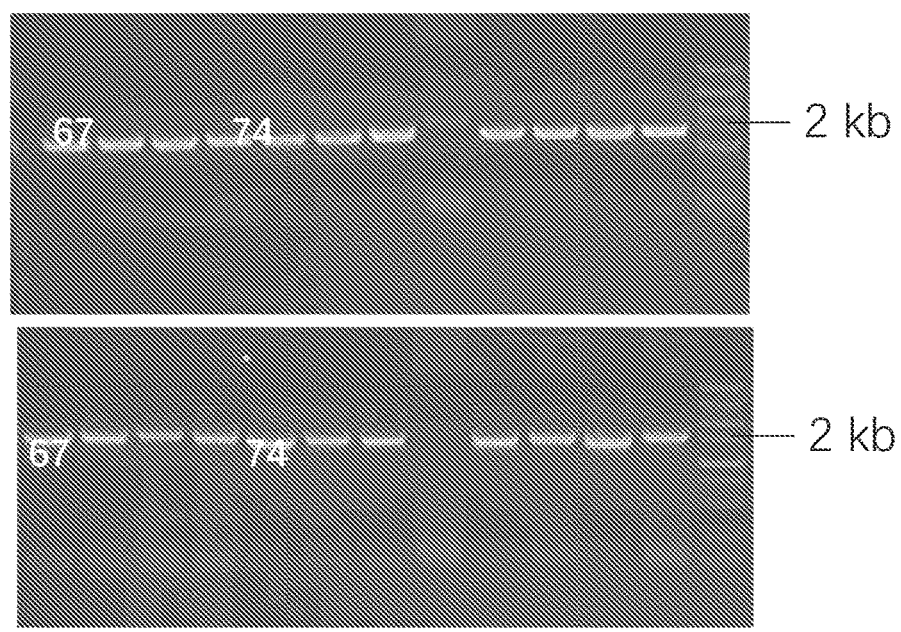
Figure 5:
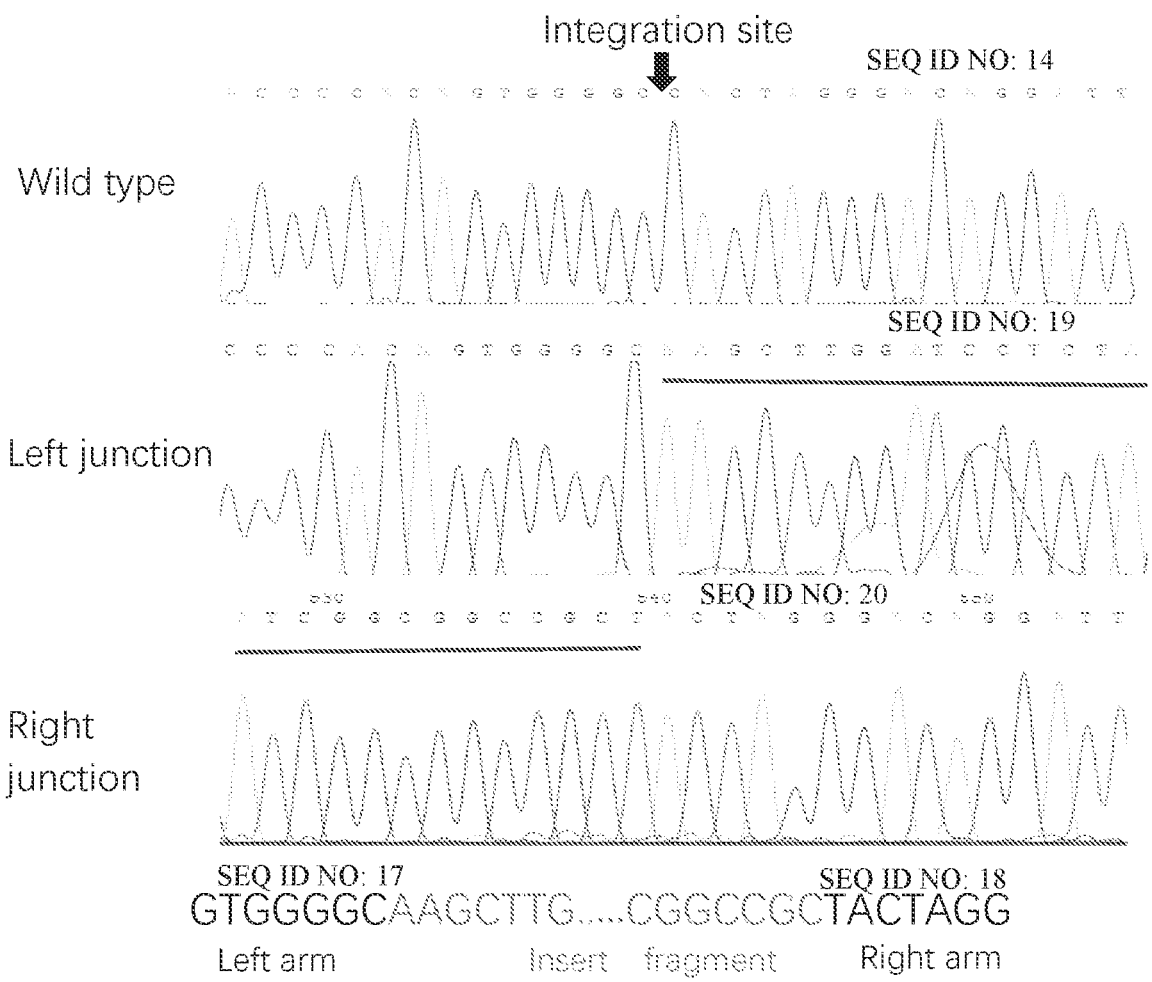
Figure 5:
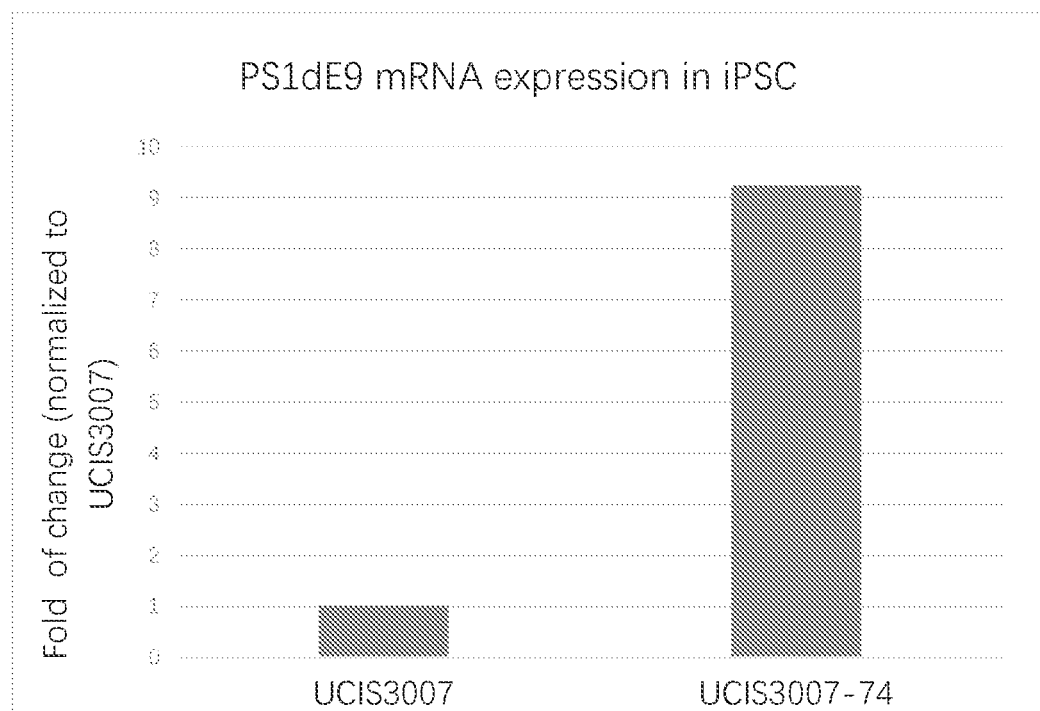

For introducing AD-related genes into AAVS1 site, parental hiPSC was cultured with mTeSR1 (Stemcell Technologies, cat. no. 05850) on a six well plate coated with Matrigel (Corning, Cat. no. 354277) at 37° C., 5% C02. Cells were harvested at 80% confluence and were co-transfected with Cas9-sgRNA plasmid and donor plasmid by electroporelation method (Amaxa Nucleofector II, program A-024). The number of cells for each transfection reaction was 0.5 to $1\times10^6$, and the amount of plasmids was: Cas9-sgRNA 2.5 µg and donor plasmid 4 µg. The transfected cells were immediately inoculated into a six-well plate coated with Matrigel, incubated with mTeSR1 and 10 uM Y-27632 (Sigma, cat. No. Y0503). After 48-hour incubation, 0.5 µg/ml of Puromycin (Xiya Reagent, cat. No. 1014553) was added to culture media for 24 hours for drug selection. Single cell clones were prepared by inoculating Puromycin-resistant cells onto Matrigel-coated T25 flasks at a density of 1000 cells/ml, incubated with mTeSR1 and 10 uM Y-27632. Single-cell clones were picked up 10 days later with assistant of microscopy and then transferred to 96-well plates coated with Matrigel. Each clone was divided into two aliquots and was cultured on two 96-well plates, one for propagation and one for identification. To verify gene integration, cells were lysed by DNA lysis kit (QuickExtract™ DNA Extraction Solution 1.0, Epicentre, Cat. #QE09050) and then presence of insert was identified by junction PCR (FIG. 4B). Positive clones identified by junction PCR were further verified by sequencing (FIG. 4C). In addition, selected clones were also subjected to pluripotency test and karyotyping to eliminate variation introduced by the single cell cloning process (FIG. 4D). Two hiPSC lines that constitutively overexpress BACE1 and PS1dE9 gene were created using a similar strategy (FIG. 4A and FIG. 5A).

Example 4: Large Scale Production of Neuronal Cells

Figure 6:
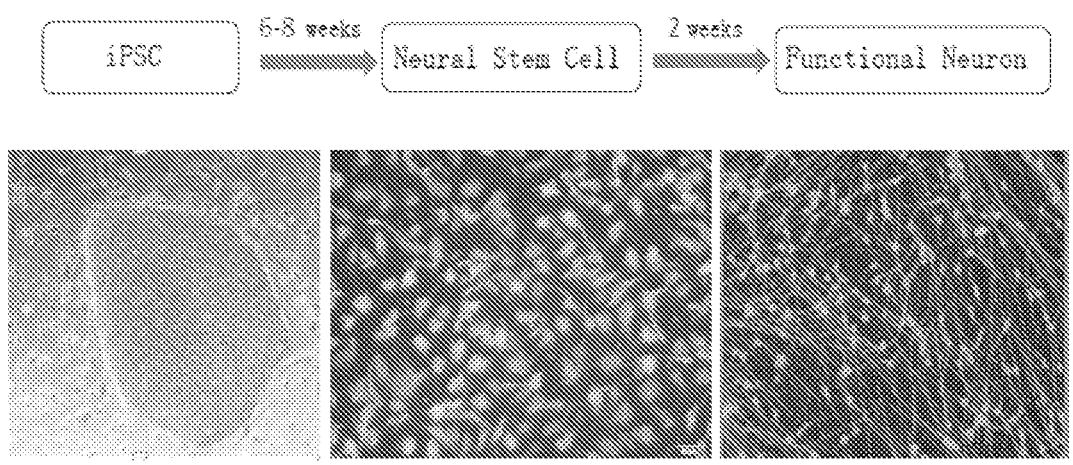
FIG. 6. Manufacturing process for making large quantities of neuronal cells from hiPSC, showing that having neural stem cells (NSCs) as an intermediate stage is a critical step for shortening the assay process and reducing variation.

As described above, being able to make large quantities of AD-relevant human neurons consistently and reproducibly is pivotal for building a physiological cellular platform for drug screening. In the current art, differentiation of hiPSC into functional neurons involves a lengthy process and is subjected to a series of changes of culture conditions. Therefore, directly seeding hiPSC in 96-well plate to make neurons will result in huge well-to-well variation in terms of number and quality of differentiated neurons. Such large variation is not suitable for drug screening. To solve this problem, a step-wise process has been developed to control variations. The first step is to produce high quality neural stem cells (NSCs) from hiPSC. This step shortens the whole process from hiPSC to mature neuron by 6-8 weeks. Second step is to differentiate NSC into neuronal progenitor cell (NPC), which further reduces the differentiation time for making mature neurons. For production of NSC stock, hiPSC were inoculated on a 12-well plate containing Neural Induction Medium (Stemcell Technologies, Cat. No. 05835) and 10 uM Y-27632 (Sigma, Cat. No. Y0503). After 5 days, the embryoid body ball formed was spread on a 12-well plate coated with Matrigel, incubated in a $CO_2$ incubator at 37° C., and changed daily with Neural Induction Medium. After 7 days, NSC-like rosette was picked and transferred into 24-well plates. The medium was replaced with NSC Proliferation Medium (CIB, Cat. No. NE-0603). After 7-8 days, NSC-like cells were picked up and transferred to 48-well plates. When NSC density reaches 90% confluence, transfer them into 6-well plates for further expansion and storage. For making functional neurons, about $8\times10^4/cm^2$ NSC were transferred to a 6-well plate coated with Poly-L-Ornithine (Sigma, Cat. No. P4957) and Laminin (Sigma, Cat. No. 2020) and cultured in Neuron Induction Medium (Stemcell Technologies, Cat. No. 08500). After 7 days, change the culture medium into Neuron Maturation Medium (Stemcell Technologies, Cat. No. 08510) and continue culture for 2-3 weeks. Mature neurons were verified by immunostaining of neuron-specific biomarkers such as Tuj1 (FIG. 6).

Example 5: Over-Expression of Beta Scretase in Modified hiPSC Line

As described above, two hiPSC lines have been made using the vectors created by the present invention. One hiPSC line (iPSN0041-21) contains a constitutively expressed BACE1 gene at AAVS1 site. For this line, expression of BACE1 gene at RNA and protein levels has been compared with those of its isogenic parental line (iPSN0041). For quantification of BACE1 mRNA expression, total RNA was extracted with TRIzol (Sigma, cat. No. T9424). qPCR was carried out using ABITM 7500 system and the fluorescent dye SYBR Premix EXTaqTMII (TaKaRa, cat. no. RR820A). The house keeping gene beta-actin was used as reference and each data point was average of three repeats. The result showed that BACE1 mRNA expression of iPSN0041-21 is much higher in iPSC and in iPSC-derived neurons compared to those of iPSN0041, indicating that the transgenic BACE1 gene is indeed constitutively over-expressed in iPSN0041-21 (FIG. 7A). Expression of BACE1 protein was carried out using an ELISA kit (Thermo Fisher, Cat. No. P0013). iPSN0041 and mature neurons were obtained using the method described above, the cells were lysed by protein lysis buffer (Biyuntian Biotechnology, Cat. No. P0013) and BACE1 protein concentration was measured using the ELISA kit according to manufacturer's instruction. Similar to the RNA result, BACE1 protein (Beta-secretase 1) level in iPSN0041-21 is significantly higher than that of the parental line iPSN0041 in hiPSC-derived NSC and neurons (FIG. 7B)

Example 6: Expression of Abeta-42 Peptides in Modified hiPSC Line

For Abeta-42 peptides detection, mature neurons were cultured in Neuron Maturation Medium (Stemcell Technologies, Cat. No. 08510) for up to 7 weeks. Supernatant was collected at 1 week intervals. Concentration of Abeta-42 peptides was measured using the Human/rat A42 ELISA kit (WAKO, Cat. No. 290-62601). For normalization, total protein from each collection was also measured (Thermo-Fisher, Pierce BCA Protein Assay Kit, Cat. No. 23225). As expected, a much higher expression of Abeta-42 peptides in iPSN0041-21 neuron culture was observed compared to those of iPSN0041 neurons (FIG. 8A). Further study over a six-week period of time showed that neurons derived from iPSN0041-21 have a different expression pattern compared to that of iPSN0041-derived neurons. Abeta-42 peptide level in iPSN0041-derived neurons (wild type) was very low at the first week of neuron culture and increased over time with a peak at the fifth week and decreased at the sixth week; whereas Abeta-42 expression in neurons derived from iPSN0041-21 was high at the first two weeks of neuron culture and decreased over time (FIG. 8B). Since neuronal cell culture in vitro for six weeks mimics the aging process of mature neurons, our observation suggested that for the wild type neurons, Abeta-42 level increased during the aging process of neurons, which is consistent with the disease mechanism for AD. The drop of Abeta-42 at sixth week might be due to neuron death in the culture. On the other hand, the high level expression of Abeta-42 in iPSN0041-21 neurons at early stage can be explained as over-expression of BACE1 transgene and the decrease in Abeta-42 expression after 3 weeks could be due to pre-mature neuron dysfunction or death as a result of too much beta-secretase. This observation suggested that elevated beta-secretase expression is harmful for neuron survival.

Example 7: Screening of Drug Compounds Using Modified hiPSC Lines

Large quantities of neuron progenitor cells (NPCs) have been produced from the modified hiPSC line IPSN0041-21. To conduct compound screening assay, NPCs were seeded in 96-well plates with a cell density at 50,000 cells/well. NPCs were cultured in Neuron Maturation Medium (Stemcell Technologies, Cat. No. 08510) for up to 4 weeks. Supernatant were collected at one-week intervals. Abeta-40 and Abeta-42 concentrations were measured at two, three, or four weeks using the Human/rat Aβ42 ELISA kit (WAKO, Cat. No. 290-62601). Compounds to be tested were added to neuron culture medium one week before measurement of Abeta-40 and Abeta-42 peptides. As shown in FIGS. 9A-9C, effect of two novel chemical compounds (B3 and B16) on Abeta peptide production were tested. The result showed that B3 and B16 reduce production of both Abeta-40 and Abeta-42 peptides, but did not affect the Abeta-42 vs. Abeta-40 ratio. One interesting notion was that the positive control, a commonly used beta-secretase inhibitor (Sigma-Aldrich, cat #S4562), disproportionally reduced production of Abeta-40 peptides as indicated by a higher Abeta-42 vs. Abeta-40 ratio compared to those of B3 and B16 treatment. This observation suggested that elevated expression of Abeta peptides in IPSN0041-21 due to over-expression of BACE1 gene indeed increases assay sensitivity of Abeta-40 and Abeta-42 peptides measurement, which allows differentiation of effect of potential drug compounds on different classes of Abeta peptides. In particularly, the system enables screening of compounds that are more effective for reduction of Abeta-42 production.

CONCLUSION

The present invention described creation of physiologically relevant cellular models for AD by over-expression of AD-related genes, e.g. BACE1 and PS1 and variants thereof in hiPSC. Several unique donor vectors have been created for targeted integration of AD-related genes at a safe harbor site (AAVS1) in human genome with high efficiency. Targeted integration of AD-related genes at AAVS1 site provides a safe and controlled transgene expression that overcomes drawbacks of commonly used random integration method, such as unknown copy numbers and potential disruption to endogenous genes. hiPSC lines created by those donor vectors display high level of beta-seretase activity and/or high level of Abeta-42 peptides that is the major component for amyloid plaque formation. A novel cellular assay platform has been established using neuronal cells derived from hiPSC lines over-expressing AD-related genes. Preliminary screening of potential drug candidate compounds indicated that the cellular platform created by the present invention offers clear advantages for screening new beta-seretase inhibitors and/or Abeta-42 peptides inhibitors compared to current art in the field.

REFERENCE

1) Heritability of different forms of memory in the Late Onset Alzheimer's Disease Family Study . . . Journal of Alzheimer's Disease. 2011; 23(2):249-55.
2) Role of genes and environments for explaining Alzheimer disease. Arch. Gen. Psychiatry. 2006; 63(2):168-74. doi: 10.1001/archpsyc.63.2.168.
3) Alzheimer's Disease. Lancet. 2006; 368(9533):387-403. doi:10.1016/S0140-6736(06)69113-7.
4) Genome-wide association studies in Alzheimer disease. Archives of Neurology. 2008; 65(3):329-34.doi:10.1001/archneur.65.3.329.
5) Selkoe D J. Translating cell biology into therapeutic advances in Alzheimer's disease. Nature. 1999; 399(6738 Suppl):A23-31.
6) Apolipoprotein E: high-avidity binding to beta-amyloid and increased frequency of type 4 allele in late-onset familial Alzheimer disease. Proceedings of the National Academy of Sciences of the United States of America. 1993; 90(5):1977-81.
7) Apolipoprotein E4: a causative factor and therapeutic target in neuropathology, including Alzheimer's disease. Proceedings of the National Academy of Sciences of the United States of America. 2006; 103(15):5644-51.
8) Variant of TREM2 associated with the risk of Alzheimer's disease. The New England Journal of Medicine. 2012; 368(2):107-16.
9) TREM2 variants in Alzheimer's disease. The New England Journal of Medicine. 2012; 368(2):117-27.
10) Tanzi, R. E. & Bertram, L. Twenty years of the Alzheimer's disease amyloid hypothesis: a genetic perspective. Cell 120: 545-555 (2005).
11) Michel, G. et al. A Century of Alzheimer's Disease. Science 314: 777-781 (2006).
12) Crews, L. & Masliah, E. Molecular mechanisms of neurodegeneration in Alzheimer's disease. Hum. Mol. Genet. 19 (R1): R12-R20 (2010).
13) Muratore, C. R. et al. The familial Alzheimer's disease APPV717I mutation alters APP processing and Tau expression in iPSC-derived neurons. Hum Mol Genet. 23 (13): 3523-3536(2014).
14) Musiek, E. S. & Holtzman, D. M. Three Dimensions of the Amyloid Hypothesis: Time, Space, and "Wingmen". Nat Neurosci 18(6): 800-806 (2016).
15) Fukumoto, H. et al. Beta-secretase protein and activity are increased in the neocortex in Alzheimer disease. Arch Neurol 59: 1381-9 (2002).
16) Yang, L. B. et al. Elevated beta-secretase expression and enzymatic activity detected in sporadic Alzheimer disease. Nat Med. 9: 3-4 (2003).
17) Li, R. et al. Amyloid beta peptide load is correlated with increased beta-secretase activity in sporadic Alzheimer's disease patients. Proc. Natl Acad. Sci. USA 101: 3632-3637(2004).
18) Willem M, Garratt A N, Novak B, Citron M, Kaufmann S, Rittger A, DeStrooper B, Saftig P, Birchmeier C, Haass C (October 2006). "Control of peripheral nerve myelination by the beta-secretase BACE1". Science. 314 (5799): 664-6.
19) Evin, G. & Hinc, C. BACE1 as a therapeutic target in Alzheimer's disease: rationale and current status. Drugs Aging 30(10): 755-64 (2013).
20) Ghosh, A. K., Brindisi, M. & Tang, J. Developing β-secretase inhibitors for treatment of Alzheimer's disease. J Neurochem 120(Suppl 1): 71-83 (2013).
21) Ghosh, A. K. & Tang, J. Prospects of β-Secretase Inhibitors for the Treatment of Alzheimer's Disease. Chem Med Chem 10(9): 1463-1466 (2015).
22) Menting, K. W. & Claassen, J. A. H. R. β-secretase inhibitor; a promising novel therapeutic drug in Alzheimer's disease. Front Aging Neurosci 6: 165 (2014).

23) Nie, Q., Du, X. G. & Geng, M. Y. Small molecule inhibitors of amyloid β peptide aggregation as a potential therapeutic strategy for Alzheimer's disease. Acta Pharmacologica Sinica 32: 545-551 (2011).
24) Habchi, J. et al. Systematic development of small molecules to inhibit specific microscopic steps of Aβ42 aggregation in Alzheimer's disease. Proc. Natl Acad. Sci. USA 114:E200-E208(2016).
25) Crunkhorn, S. Identification of novel A inhibitors. Nature Reviews Drug Discovery 16: 88 (2017).
26) Vassar, R. BACE1 inhibitor drugs in clinical trials for Alzheimer's disease. Alzheimer's Research & Therapy 6: 89 (2014).
27) Higgins, G. A. & Jacobsen, H. Transgenic mouse models of Alzheimer's disease: phenotype and application. Behavioural Pharmacology 14: 419-438 (2003).
28) Takahashi, K. & Yamanaka, S. Induction of Pluripotent Stem Cells from Mouse Embryonic and Adult Fibroblast Cultures by Defined Factors. Cell 126 (4): 663-676 (2006).
29) Takahashi, K. et al. Induction of pluripotentstem cells from adult human fibroblasts by defined factors. Cell 131 (5): 861-872 (2007).
30) Yagi, T. et al. Modeling familial Alzheimer's disease with induced pluripotent stem cells. Hum. Mol. Genet. 20: 4530-4539 (2011).
31) Israel, M. A. et al. Probing sporadic and familial Alzheimer's disease using induced pluripotent stem cells. Nature 482: 216-220 (2012).
32) Young, J. E. & Goldstein, L. S. B. Alzheimer's disease in a dish: promises and challenges of human stem cell models. Hum. Mol. Genet. 21(R1): R82-R89 (2012).
33) Kondo, T. et al. Modeling Alzheimer's disease with iPSCs reveals stress phenotypes associated with intracellular Ab and differential drug responsiveness. Cell Stem Cell 12:487-496(2013).
34) Muratore, C. R. et al. The familial Alzheimer's disease APPV717I mutation alters APP processing and Tau expression in iPSC-derived neurons. Hum. Mol. Genet. 23: 3523-3536(2014).
35) Sproul, A. A. et al. Characterization and molecular profiling of PSEN1 familial Alzheimer's disease iPSC-derived neural progenitors. PLoS ONE 9: e84547 (2014).
36) Young, J. E. et al. Elucidating molecular phenotypes caused by the SORL1 Alzheimer's disease genetic risk factor using human induced pluripotent stem cells. Cell Stem Cell 16 (4): 373-385 (2015).
37) Okabe M, Ikawa M, Kominami K, Nakanishi T, Nishimune Y. 'Green mice' as a source of ubiquitous green cells. FEBS Lett. 1997 May 5; 407(3):313-9.
38) Alexopoulou A N, Couchman J R, and Whiteford J R. The CMV early enhancer/chicken beta actin (CAG) promoter can be used to drive transgene expression during the differentiation of murine embryonic stem cells into vascular progenitors. BMC Cell Biology 9: 2, 2008.
39) M W McBurney, L C Sutherland, C N Adra, B Leclair, M A Rudnicki, and K Jardine, The mouse Pgk-1 gene promoter contains an upstream activator sequence, Nucleic Acids Res. 1991 Oct. 25; 19(20):5755-5761.
40) Hsu, P. D., Lander, E. S. and Zhang, F. Development and Applications of CRISPR-Cas9 for Genome Engineering. Cell 157: 1262-1278 (2014).
41) Cong, L. et al. Multiplex Genome Engineering Using CRISPR/Cas Systems. Science 339 (6121):819-823 (2013).
42) Ran, F. A. et al. Genome engineering using the CRISPR-Cas9system. Nature Protocols 8:2281-2308(2013).
43) Wang, J. et al. Generation of clinical-grade human pluripotent stem cells in Xeno-free conditions. Stem Cell Research & Therapy, (6): 223 (2015).
44) Zhou, T. et al. Generation of human induced pluripotent stem cells from urine samples. Nat Protoc. 7(12): 2080-2089 (2012).

The invention claimed is:

1. A method of generating a cellular model of Alzheimer's disease (AD), comprising integrating an AD-related gene into human induced pluripotent stem cells hiPSCs to induce increased expression of beta-secretase and/or Abeta-42 peptides as compared to the expression level of beta-secretase and/or Abeta-42 peptides in isogenic hiPSCs without integration of the AD-related gene,
   wherein the AD-related gene is integrated into the hiPSC at the adeno-associated virus integration site 1 (AAVS1) site;
   wherein the AD-related gene is integrated into the hiPSCs by a mammalian expression vector comprising a nucleotide acid sequence encoding an AD-related protein and a reporter, wherein the nucleotide acid sequence is operably linked with a promoter for driving a high level of gene expression in the mammalian expression vector, wherein the promoter is CAG promoter; and
   wherein the AD-related gene is beta-secretase 1 (BACE1) gene and is constitutively overexpressed in hiPSCs.

2. A cellular model of Alzheimer's disease (AD) generated by the method of claim 1.

3. A high throughput method for screening a therapeutic agent for treatment of AD, comprising:
   i) Preparing a cellular model of Alzheimer's disease (AD) from a hiPSC by introducing an expression vector or a genetic construct to the hiPSC, wherein the expression vector comprises a nucleic acid sequence encoding an AD-related protein selected from the group consisting of mutant APP attributing to the onset of AD, PS1dE9 and BACE1 and a reporter, wherein the nucleic acid sequence is operably linked to a promoter for driving high level of gene expression in a mammalian expression vector, and
   wherein the genetic construct comprises a nucleic acid sequence coding for: a first promoter;
   a drug selection gene controlled by the first promoter; a second promoter; an AD-related gene linked to a reporter gene controlled by the second promoter; and sequence homologous to human AAVS1 site, wherein all said elements are in a cis order, wherein the AD-related gene is selected from the group consisting of mutant APP attributing to the onset of AD, PS1dE9 gene and BACE1 gene;
   ii) Culturing the candidate compounds with the cellular model for two days to two weeks, and
   iii) measuring beta-secretase level, Abeta-42 concentration, and Abeta42/Abeta-40 ratio before and after adding the candidate compounds;
   wherein reduction of one or more measurements selected from beta-secretase level, Abeta-42 concentration and Abeta42/Abeta-40 ratio indicates the candidate compound is a potential therapeutic agent for treatment of AD.

4. The method of claim 3, the hiPSCs come from a human donor and are converted to hiPSC by a conventional reprogramming method in vitro.

5. The method of claim 4, the hiPSCs come from a normal human donor without AD and are converted to hiPSC by a conventional reprogramming method in vitro.

6. The method of claim 3, which is for screening of early AD drug.

7. A drug screening process for screening beta-secretase or Abeta-42 inhibitor, comprising
   i) modifying hiPSC line by constitutively over-expressing BACE1 gene, wherein the hiPSC line is produced by introducing a mammalian expression vector to the hiPSC, wherein the expression vector comprises a nucleic acid sequence encoding an AD-related protein and a reporter, wherein the nucleotide acid sequence is operably linked with a promoter for driving a high level of gene expression in the mammalian expression vector, wherein the promoter is CAG promoter; and wherein the AD-related gene is integrate into the hiPSC at AAVS1 site,
   ii) re-differentiating hiPSC line into functional neurons,
   iii) culturing the functional neurons in presence of candidate drug compounds, and
   iv) measuring beta-secretase level, Abeta-42/Abeta-40 ratio, and/or Abeta-42 concentration and selecting compounds that can reduce beta-secretase level, Abeta-42/Abeta-40 ratio, and/or Abeta-42 concentration.

8. The process of claim 7, comprising culturing the functional neurons in presence of candidate drug compounds for two days to two weeks.

9. The-process of claim 7, the hiPSCs come from a human donor and are converted to hiPSC by a conventional reprogramming method in vitro.

10. The-process of claim 9, the hiPSCs come from a normal human donor without AD and are converted to hiPSC by a conventional reprogramming method in vitro.

11. The process of claim 7, wherein the expression vector further comprises a nucleic acid sequence encoding a drug selection gene controlled by a promoter for driving high level of gene expression in a mammalian expression vector.

12. The process of claim 11, wherein the drug selection gene is antibiotic resistance gene.

13. The process of claim 7, wherein all the elements in the vector are in an order beneficial to expression of the AD-related gene.

* * * * *

SEQUENCE LISTING

```
<160> NUMBER OF SEQ ID NOS: 115

<210> SEQ ID NO 1
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 1
gtacggggcg atcatccaca                                                   20

<210> SEQ ID NO 2
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 2
aatcgactcg aacttcgtgt                                                   20

<210> SEQ ID NO 3
<211> LENGTH: 22
<212> TYPE: DNA
<213> ORGANISM: Homo sapiens
```

<400> SEQUENCE: 3
agcggagagc cctcggcatc gg                                            22

<210> SEQ ID NO 4
<211> LENGTH: 23
<212> TYPE: DNA
<213> ORGANISM: Homo sapiens

<400> SEQUENCE: 4
tgctcatctg cgccgggcaa ggg                                           23

<210> SEQ ID NO 5
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 5
aagcggagga caggattggg                                               20

<210> SEQ ID NO 6
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 6
cctctgtggc cctggagatg                                               20

<210> SEQ ID NO 7
<211> LENGTH: 22
<212> TYPE: DNA
<213> ORGANISM: Homo sapiens

<400> SEQUENCE: 7
gactggcgag agcctggagc gg                                            22

<210> SEQ ID NO 8
<211> LENGTH: 22
<212> TYPE: DNA
<213> ORGANISM: Homo sapiens

<400> SEQUENCE: 8
cggaccagct gctaccccta gg                                            22

<210> SEQ ID NO 9
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 9
gccgcttcga aagtgactgg                                               20

<210> SEQ ID NO 10
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 10

-continued

```
gatcccccag tgcccatcag                                              20

<210> SEQ ID NO 11
<211> LENGTH: 23
<212> TYPE: DNA
<213> ORGANISM: Homo sapiens

<400> SEQUENCE: 11
ccagaatgca cagatgtctg agg                                          23

<210> SEQ ID NO 12
<211> LENGTH: 22
<212> TYPE: DNA
<213> ORGANISM: Homo sapiens

<400> SEQUENCE: 12
ttcatggcct ctgacagcga gg                                           22

<210> SEQ ID NO 13
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 13
tggtgtctca ggcggttcta                                              20

<210> SEQ ID NO 14
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 14
tgaactatga ggcgctgcac                                              20

<210> SEQ ID NO 15
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 15
tgactttcgt ggctatgcgt                                              20

<210> SEQ ID NO 16
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 16
ctagcaccca ggcatccaaa                                              20

<210> SEQ ID NO 17
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE
```

<400> SEQUENCE: 17
gagagtgact cccgttgtcc                                                  20

<210> SEQ ID NO 18
<211> LENGTH: 24
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 18
acattgcaaa cacaggaaat tgag                                             24

<210> SEQ ID NO 19
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 19
gtgttgagtt tccggcgttc                                                  20

<210> SEQ ID NO 20
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 20
tcgcttgttc tggctgatgt                                                  20

<210> SEQ ID NO 21
<211> LENGTH: 24
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 21
gcactctccc aaaacagtat ctta                                             24

<210> SEQ ID NO 22
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 22
gtgcctccac ccagatcaaa                                                  20

<210> SEQ ID NO 23
<211> LENGTH: 20
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 23
gggtgaggcg caaaaggata                                                  20

<210> SEQ ID NO 24
<211> LENGTH: 20

```
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 24
acaccagcgt caatggagag                                                    20

<210> SEQ ID NO 25
<211> LENGTH: 23
<212> TYPE: DNA
<213> ORGANISM: Artificial sequence
<220> FEATURE:
<223> OTHER INFORMATION: PAM sequence

<400> SEQUENCE: 25
gtacggggcg atcatccaca cgg                                                23

<210> SEQ ID NO 26
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 26
gcaaaagtgg cataaaaccg cgg                                                23

<210> SEQ ID NO 27
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 27
tatcgcttcc gattagtccg cgg                                                23

<210> SEQ ID NO 28
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 28
ctatctcgag tggtaatgcg cgg                                                23

<210> SEQ ID NO 29
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 29
gtagctgctg taaatcgcat cgg                                                23

<210> SEQ ID NO 30
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 30
```
tataccagac cacagcgccg cgg                                    23

<210> SEQ ID NO 31
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 31
gcacgaggtg aacagccgct cgg                                    23

<210> SEQ ID NO 32
<211> LENGTH: 23
<212> TYPE: DNA
<213> ORGANISM: Artificial sequence
<220> FEATURE:
<223> OTHER INFORMATION: Artificially synthesized sequence

<400> SEQUENCE: 32
atgatatctg acatgcagcg cgg                                    23

<210> SEQ ID NO 33
<211> LENGTH: 23
<212> TYPE: DNA
<213> ORGANISM: Artificial sequence
<220> FEATURE:
<223> OTHER INFORMATION: Artificially synthesized sequence

<400> SEQUENCE: 33
aatcgactcg aacttcgtgt cgg                                    23

<210> SEQ ID NO 34
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 34
cgaatcggaa ctttgtaccg cgg                                    23

<210> SEQ ID NO 35
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 35
accgagcgga gagccctcgg cat                                    23

<210> SEQ ID NO 36
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 36
aaacatgccg agggctctcc gct                                    23

<210> SEQ ID NO 37
<211> LENGTH: 24
<212> TYPE: DNA
<213> ORGANISM: Artificial Sequence

```
<220> FEATURE:
<223> OTHER INFORMATION: ARTIFICIALLY SYNTHESIZED SEQUENCE

<400> SEQUENCE: 37
accgtgctca tctgcgccgg gcaa                                          24

<210> SEQ ID NO 38
<211> LENGTH: 24
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 38
aaacttgccc ggcgcagatg agca                                          24

<210> SEQ ID NO 39
<211> LENGTH: 58
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 39
tatacgtctc aaccgagcgg agagccctcg gcatgtttaa gagctatgct ggaaacag     58

<210> SEQ ID NO 40
<211> LENGTH: 56
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 40
tatacgtctc aaaacttgcc cggcgcagat gagcacggtg tttcgtcctt tccaca       56

<210> SEQ ID NO 41
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 41
accggactgg cgagagcctg gag                                           23

<210> SEQ ID NO 42
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 42
aaacctccag gctctcgcca gtc                                           23

<210> SEQ ID NO 43
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 43
accgcggacc agctgctacc cct                                           23
```

<210> SEQ ID NO 44
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 44 aaacagggt agcagctggt ccg                                            23

<210> SEQ ID NO 45
<211> LENGTH: 58
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 45
tatacgtctc aaccggactg gcgagagcct ggaggtttaa gagctatgct ggaaacag    58

<210> SEQ ID NO 46
<211> LENGTH: 55
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 46
tatacgtctc aaaacagggg tagcagctgg tccgcggtgt ttcgtccttt ccaca       55

<210> SEQ ID NO 47
<211> LENGTH: 24
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 47
accgccagaa tgcacagatg tctg                                          24

<210> SEQ ID NO 48
<211> LENGTH: 24
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 48
aaaccagaca tctgtgcatt ctgg                                          24

<210> SEQ ID NO 49
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 49
accgttcatg gcctctgaca gcg                                           23

<210> SEQ ID NO 50
<211> LENGTH: 23
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 50
aaaccgctgt cagaggccat gaa                                          23

<210> SEQ ID NO 51
<211> LENGTH: 58
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 51
tatacgtctc aaccgccaga atgcacagat gtctggttta agagctatgc tggaaaca    58

<210> SEQ ID NO 52
<211> LENGTH: 55
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 52
tatacgtctc aaaaccgctg tcagaggcca tgaacggtgt ttcgtccttt ccaca       55

<210> SEQ ID NO 53
<211> LENGTH: 22
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 53
accgcaggag taggtggtgc cc                                           22

<210> SEQ ID NO 54
<211> LENGTH: 22
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 54
aaacgggcac cacctactcc tg                                           22

<210> SEQ ID NO 55
<211> LENGTH: 59
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 55
agagccctcg gcatcggctt ccagtggctc tctttggtta gtcacctact agttagtca   59

<210> SEQ ID NO 56
<211> LENGTH: 42
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 56
ggcttaggat tgttacgccc tcacttatct actaatcaat ta                     42

<210> SEQ ID NO 57

<211> LENGTH: 57
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 57
tccactgcga cgtcgcgagt agcggagagc cctcggcatc ggcttccagt ggctctc      57

<210> SEQ ID NO 58
<211> LENGTH: 59
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 58
tctgcgccgg gcaaggggga cgcagggagg atggggggtta gtcacctact agttagtca   59

<210> SEQ ID NO 59
<211> LENGTH: 58
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 59
tccactgcga cgtcgcgagt tgctcatctg cgccgggcaa ggggggacgca gggaggat    58

<210> SEQ ID NO 60
<211> LENGTH: 59
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 60
cccggcgcag atgagcacca gagtggccaa agagagctca cttatctact aatcaatta    59

<210> SEQ ID NO 61
<211> LENGTH: 52
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 61
ggcttaggat tgttacgccc cccttgcccg gcgcagatga gcaccagagt gg            52

<210> SEQ ID NO 62
<211> LENGTH: 59
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 62
gcgagagcct ggagcggctt cggagagggc tagctgctta gtcacctact agttagtca    59

<210> SEQ ID NO 63
<211> LENGTH: 56
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 63
tccactgcga cgtcgcgagt gactggcgag agcctggagc ggcttcggag agggct        56

<210> SEQ ID NO 64
<211> LENGTH: 58
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 64
agctgctacc cctaggaggc ggccgggacc ggaaagttag tcacctacta gttagtca        58

<210> SEQ ID NO 65
<211> LENGTH: 59
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 65
tccactgcga cgtcgcgagt cggaccagct gctacccta ggaggcggcc gggaccgga        59

<210> SEQ ID NO 66
<211> LENGTH: 59
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 66
gggtagcagc tggtccgtgg atacagtggg agggtcctca cttatctact aatcaatta        59

<210> SEQ ID NO 67
<211> LENGTH: 56
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 67
ggcttaggat tgttacgccc cctaggggta gcagctggtc cgtggataca gtggga        56

<210> SEQ ID NO 68
<211> LENGTH: 53
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 68
gatgtctgag gacaaccacc tgagcaatac tttagtcacc tactagttag tca        53

<210> SEQ ID NO 69
<211> LENGTH: 54
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 69
tccactgcga cgtcgcgagt ccagaatgca cagatgtctg aggacaacca cctg        54

<210> SEQ ID NO 70
<211> LENGTH: 54
<212> TYPE: DNA

<213> ORGANISM: Artificial Sequence
<220> FEATURE:
<223> OTHER INFORMATION: ARTIFICIALLY SYNTHESIZED SEQUENCE

<400> SEQUENCE: 70
ctgacagcga ggaagaagtg tgtgatgagc ggttagtcac ctactagtta gtca    54

<210> SEQ ID NO 71
<211> LENGTH: 50
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 71
tccactgcga cgtcgcgagt ttcatggcct ctgacagcga ggaagaagtg    50

<210> SEQ ID NO 72
<211> LENGTH: 55
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 72
ggcttaggat tgttacgccc cctcgctgtc agaggccatg aatgtgagca tagcc    55

<210> SEQ ID NO 73
<211> LENGTH: 50
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 73
gccatgaatg tgagcatagc cctgcctctc acttatctac taatcaatta    50

<210> SEQ ID NO 74
<211> LENGTH: 56
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 74
accacctact cctgcgtggg ggtgttccaa cacgttagtc acctactagt tagtca    56

<210> SEQ ID NO 75
<211> LENGTH: 54
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 75
tccactgcga cgtcgcgagt cctgggcacc acctactcct gcgtgggggt gttc    54

<210> SEQ ID NO 76
<211> LENGTH: 61
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 76
cgaagagtaa ccgttgctag gagagaccgt ggctgaatga gactggtgtc gacactagtg    60

```
g                                                             61

<210> SEQ ID NO 77
<211> LENGTH: 48
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 77
cgcgccacta gtgtcgacac cagtctctaa ttttttttt caaaaaaa            48

<210> SEQ ID NO 78
<211> LENGTH: 28
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 78
cgaagagtaa ccgttgctag gagagacc                                 28

<210> SEQ ID NO 79
<211> LENGTH: 25
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 79
gtggctgaat gagactggtg tcgac                                    25

<210> SEQ ID NO 80
<211> LENGTH: 24
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 80
gcaacctccc cttctacgag cggc                                     24

<210> SEQ ID NO 81
<211> LENGTH: 24
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 81
gcatggccgt gttgagcggt tccc                                     24

<210> SEQ ID NO 82
<211> LENGTH: 51
<212> TYPE: DNA
<213> ORGANISM: Homo sapiens

<400> SEQUENCE: 82
taatctggga gcctgcccta cttccagaat gcacagatgt ctgaggacaa c        51

<210> SEQ ID NO 83
<211> LENGTH: 50
<212> TYPE: DNA
<213> ORGANISM: Artificial sequence
<220> FEATURE:
```

```
<223> OTHER INFORMATION: Artificially synthesized sequence
<220> FEATURE:
<221> NAME/KEY: mutation
<222> LOCATION: (28)..(29)
<223> OTHER INFORMATION: A  base deletion between the two bases
<220> FEATURE:
<221> NAME/KEY: mutation
<222> LOCATION: (38)..(39)
<223> OTHER INFORMATION: A  base deletion between the two bases

<400> SEQUENCE: 83
taatctggga gcctgccta cttccagaat gcacagattc tgaggacaac          50

<210> SEQ ID NO 84
<211> LENGTH: 13
<212> TYPE: DNA
<213> ORGANISM: Artificial sequence
<220> FEATURE:
<223> OTHER INFORMATION: Artificially synthesized sequence

<400> SEQUENCE: 84
taatctggga gcc                                                  13

<210> SEQ ID NO 85
<211> LENGTH: 12
<212> TYPE: DNA
<213> ORGANISM: Artificial sequence
<220> FEATURE:
<223> OTHER INFORMATION: Artificially synthesized sequence

<400> SEQUENCE: 85
tctgaggaca ac                                                   12

<210> SEQ ID NO 86
<211> LENGTH: 33
<212> TYPE: DNA
<213> ORGANISM: Homo sapiens

<400> SEQUENCE: 86
ctcacattca tggcctctga cagcgaggaa gaa                             33

<210> SEQ ID NO 87
<211> LENGTH: 34
<212> TYPE: DNA
<213> ORGANISM: Artificial sequence
<220> FEATURE:
<223> OTHER INFORMATION: Artificially synthesized sequence
<220> FEATURE:
<221> NAME/KEY: mutation
<222> LOCATION: (22)..(22)
<223> OTHER INFORMATION: An inserted base

<400> SEQUENCE: 87
ctcacattca tggcctctga caagcgagga agaa                            34

<210> SEQ ID NO 88
<211> LENGTH: 22
<212> TYPE: DNA
<213> ORGANISM: Artificial sequence
<220> FEATURE:
<223> OTHER INFORMATION: Artificially synthesized sequence

<400> SEQUENCE: 88
ctcacattca tggcctctga ca                                         22

<210> SEQ ID NO 89
<211> LENGTH: 12
```

```
<212> TYPE: DNA
<213> ORGANISM: Artificial sequence
<220> FEATURE:
<223> OTHER INFORMATION: Artificially synthesized sequence

<400> SEQUENCE: 89
agcgaggaag aa                                                          12

<210> SEQ ID NO 90
<211> LENGTH: 40
<212> TYPE: DNA
<213> ORGANISM: Homo sapiens

<400> SEQUENCE: 90
gttgtcctac ttccagaatg cacagatgtc tgaggacaac                             40

<210> SEQ ID NO 91
<211> LENGTH: 41
<212> TYPE: DNA
<213> ORGANISM: Artificial sequence
<220> FEATURE:
<223> OTHER INFORMATION: Artificially synthesized sequence
<220> FEATURE:
<221> NAME/KEY: mutation
<222> LOCATION: (28)..(28)
<223> OTHER INFORMATION: inserted base

<400> SEQUENCE: 91
gttgtcctac ttccagaatg cacagatgtt ctgaggacaa c                           41

<210> SEQ ID NO 92
<211> LENGTH: 30
<212> TYPE: DNA
<213> ORGANISM: Artificial sequence
<220> FEATURE:
<223> OTHER INFORMATION: Artificially synthesized sequence

<400> SEQUENCE: 92
gttgtcctac ttccagaatg cacagatgtt                                        30

<210> SEQ ID NO 93
<211> LENGTH: 28
<212> TYPE: DNA
<213> ORGANISM: Artificial sequence
<220> FEATURE:
<223> OTHER INFORMATION: Artificially synthesized sequence

<400> SEQUENCE: 93
tccagaatgc acagattctg aggacaac                                          28

<210> SEQ ID NO 94
<211> LENGTH: 20
<212> TYPE: DNA
<213> ORGANISM: Artificial sequence
<220> FEATURE:
<223> OTHER INFORMATION: Artificially synthesized sequence

<400> SEQUENCE: 94
ctcacattca tggcctctga                                                   20

<210> SEQ ID NO 95
<211> LENGTH: 36
<212> TYPE: DNA
<213> ORGANISM: Homo sapiens

<400> SEQUENCE: 95
```
cggcatcgac ctgggcacca cctactcctg cgtggg        36

<210> SEQ ID NO 96
<211> LENGTH: 36
<212> TYPE: DNA
<213> ORGANISM: Homo sapiens

<400> SEQUENCE: 96
aggcatcgac ctgggcacca cctactcctg tgtggg        36

<210> SEQ ID NO 97
<211> LENGTH: 36
<212> TYPE: DNA
<213> ORGANISM: Homo sapiens

<400> SEQUENCE: 97
cggcatcgac ctgggcacca cctattcgtg cgtcgg        36

<210> SEQ ID NO 98
<211> LENGTH: 36
<212> TYPE: DNA
<213> ORGANISM: Homo sapiens

<400> SEQUENCE: 98
gggcatcgac ctgggcacca cctactcctg cgtggg        36

<210> SEQ ID NO 99
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: n represents a, t, c or g

<400> SEQUENCE: 99
nggcatcgac ctgggcacca cctantcntg ngtngg        36

<210> SEQ ID NO 100
<211> LENGTH: 18
<212> TYPE: DNA
<213> ORGANISM: Artificial sequence
<220> FEATURE:
<223> OTHER INFORMATION: sgRNA encoding sequence

<400> SEQUENCE: 100
cccgtggtgg atgaggac        18

<210> SEQ ID NO 101
<211> LENGTH: 41
<212> TYPE: DNA
<213> ORGANISM: Homo sapiens

<400> SEQUENCE: 101
tcggcatcga cctgggcacc acctactcct gcgtgggggt g        41

<210> SEQ ID NO 102
<211> LENGTH: 16
<212> TYPE: DNA
<213> ORGANISM: Artificial sequence
<220> FEATURE:
<223> OTHER INFORMATION: Artificially synthesized sequence

<400> SEQUENCE: 102
tcggcatcga cctggg        16

<210> SEQ ID NO 103
<211> LENGTH: 25
<212> TYPE: DNA
<213> ORGANISM: Artificial sequence
<220> FEATURE:
<223> OTHER INFORMATION: Artificially synthesized sequence

<400> SEQUENCE: 103
caccacctac tcctgcgtgg gggtg                                          25

<210> SEQ ID NO 104
<211> LENGTH: 40
<212> TYPE: DNA
<213> ORGANISM: Artificial sequence
<220> FEATURE:
<223> OTHER INFORMATION: Artificially synthesized sequence
<220> FEATURE:
<221> NAME/KEY: mutation
<222> LOCATION: (16)..(17)
<223> OTHER INFORMATION: a base deletion between the two bases

<400> SEQUENCE: 104
tcggcatcga cctgggacca cctactcctg cgtggggtg                            40

<210> SEQ ID NO 105
<211> LENGTH: 41
<212> TYPE: DNA
<213> ORGANISM: Homo sapiens

<400> SEQUENCE: 105
taggcatcga cctgggcacc acctactcct gtgtgggggt g                         41

<210> SEQ ID NO 106
<211> LENGTH: 34
<212> TYPE: DNA
<213> ORGANISM: Artificial sequence
<220> FEATURE:
<223> OTHER INFORMATION: Artificially synthesized sequence
<220> FEATURE:
<221> NAME/KEY: mutation
<222> LOCATION: (9)..(10)
<223> OTHER INFORMATION: 7 bases deletion between the two bases

<400> SEQUENCE: 106
taggcatcgc accacctact cctgtgtggg ggtg                                 34

<210> SEQ ID NO 107
<211> LENGTH: 12
<212> TYPE: DNA
<213> ORGANISM: Artificial sequence
<220> FEATURE:
<223> OTHER INFORMATION: Artificially synthesized sequence

<400> SEQUENCE: 107
taggcatcga cc                                                        12

<210> SEQ ID NO 108
<211> LENGTH: 25
<212> TYPE: DNA
<213> ORGANISM: Artificial sequence
<220> FEATURE:
<223> OTHER INFORMATION: Artificially synthesized sequence

<400> SEQUENCE: 108
caccacctac tcctgtgtgg gggtg                                          25

```
<210> SEQ ID NO 109
<211> LENGTH: 41
<212> TYPE: DNA
<213> ORGANISM: Homo sapiens

<400> SEQUENCE: 109
tgggcatcga cctgggcacc acctactcgt gcgtgggcgt g                    41

<210> SEQ ID NO 110
<211> LENGTH: 29
<212> TYPE: DNA
<213> ORGANISM: Artificial sequence
<220> FEATURE:
<223> OTHER INFORMATION: Artificially synthesized sequence
<220> FEATURE:
<221> NAME/KEY: mutation
<222> LOCATION: (6)..(7)
<223> OTHER INFORMATION: 12 baseses deletion between the two bases

<400> SEQUENCE: 110
taggcaccac ctactcctgt gtggggtg                                   29

<210> SEQ ID NO 111
<211> LENGTH: 35
<212> TYPE: DNA
<213> ORGANISM: Artificial sequence
<220> FEATURE:
<223> OTHER INFORMATION: Artificially synthesized sequences
<220> FEATURE:
<221> NAME/KEY: mutation
<222> LOCATION: (10)..(11)
<223> OTHER INFORMATION: 6 bases deletion between the two sequences

<400> SEQUENCE: 111
tgggcatcga caccacctac tcgtgcgtgg gcgtg                           35

<210> SEQ ID NO 112
<211> LENGTH: 53
<212> TYPE: DNA
<213> ORGANISM: Artificial sequence
<220> FEATURE:
<223> OTHER INFORMATION: Artificially synthesized sequence

<400> SEQUENCE: 112
cgacctgggc accacctact cctgcgtggg ggtgttccaa cacggcaagg tgg       53

<210> SEQ ID NO 113
<211> LENGTH: 53
<212> TYPE: DNA
<213> ORGANISM: Artificial sequence
<220> FEATURE:
<223> OTHER INFORMATION: Artificially synthesized sequence

<400> SEQUENCE: 113
cgacctgggc accacctact cctgtgtggg ggtgttccag cacggcaagg tgg       53

<210> SEQ ID NO 114
<211> LENGTH: 53
<212> TYPE: DNA
<213> ORGANISM: Artificial sequence
<220> FEATURE:
<223> OTHER INFORMATION: Artificially synthesized sequence

<400> SEQUENCE: 114
cgacctgggc accacctact cgtgcgtggg cgtgtttcag cagggccgcg tgg       53
```

```
<210> SEQ ID NO 115
<211> LENGTH: 53
<212> TYPE: DNA
<213> ORGANISM: Artificial sequence
<220> FEATURE:
<223> OTHER INFORMATION: Artificially synthesized sequence

<400> SEQUENCE: 115
cgacctgggc accacctatt cgtgcgtcgg ggtcttccaa catggcaagg tgg            53
```